(12) United States Patent
Okuda et al.

(10) Patent No.: US 7,951,822 B2
(45) Date of Patent: May 31, 2011

(54) 1,3-DIHYDROISOBENZOFURAN DERIVATIVES

(75) Inventors: Ayumu Okuda, Tokyo (JP); Takayuki Matsuda, Tokyo (JP); Toru Miura, Tokyo (JP); Koichi Yamazaki, Tokyo (JP); Yuki Yamaguchi, Tokyo (JP); Minoru Koura, Tokyo (JP); Sayaka Kurobuchi, Tokyo (JP); Yuichiro Watanabe, Tokyo (JP); Kimiyuki Shibuya, Tokyo (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 0 days.

(21) Appl. No.: 12/413,894

(22) Filed: Mar. 30, 2009

(65) Prior Publication Data

US 2009/0247587 A1    Oct. 1, 2009

Related U.S. Application Data

(60) Provisional application No. 61/041,109, filed on Mar. 31, 2008.

(51) Int. Cl.
| | |
|---|---|
| *A61K 31/4166* | (2006.01) |
| *A61K 31/427* | (2006.01) |
| *A61K 31/422* | (2006.01) |
| *A61K 31/45* | (2006.01) |
| *A61K 31/4525* | (2006.01) |
| *C07D 405/12* | (2006.01) |
| *C07D 417/12* | (2006.01) |
| *C07D 413/12* | (2006.01) |
| *C07D 407/12* | (2006.01) |

(52) U.S. Cl. ........ 514/320; 514/337; 514/348; 514/389; 514/369; 514/376; 514/422; 548/311.4; 548/483; 548/227; 548/525; 546/296; 546/196; 546/219

(58) Field of Classification Search .................. None
See application file for complete search history.

(56) References Cited

U.S. PATENT DOCUMENTS

2005/0215577 A1   9/2005  Dehmlow et al.

FOREIGN PATENT DOCUMENTS

| EP | 199963 A1 * | 11/1986 |
|---|---|---|
| WO | 00/54759 A2 | 9/2000 |
| WO | 02/24632 A2 | 3/2002 |
| WO | 03/082192 A2 | 10/2003 |
| WO | 2004/024161 A1 | 3/2004 |
| WO | 2004/058717 A1 | 7/2004 |
| WO | 2004/072046 A2 | 8/2004 |
| WO | 2005/023188 A2 | 3/2005 |

OTHER PUBLICATIONS

Byrn et al. Solid-State Chemistry of Drugs, 2d, Chapter 11 Hydrates and Solvates, 233-247 (1999).*
Morissette et al. Adv. Drug Delivery Rev. 2004, 56, 275-300.*
Rouhi, Chem. & Eng. News, Feb. 24, 2003, 81(8), 32-35.*
Schafer et al. Drug Discovery Today, 13:913 (2008).*
Horig et al. Journal of Translational Medicine, 2:44 (2004).*
Janowski, Bethany A. et al.; "An oxysterol signalling pathway mediated by the nuclear receptor LXRα"; Nature, vol. 383, Oct. 24, 2006, pp. 728-731.
Lehmann, Jurgen M. et al.; "Activation of the Nuclear Receptor LXR by Oxysterols Defines a New Hormone Response Pathway"; The Journal of Biological Chemistry, vol. 272, No. 6, Feb. 7, 1997, pp. 3137-3140.
Fu, Xuan et al.; "27-Hydroxycholesterol Is an Endogenous Ligand for Liver X Receptor in Cholestrol-loaded Cells"; The Journal of Biological Chemistry, vol. 276, No. 42, Oct. 19, 2001, pp. 38378-38387.
Zelcer, Noam et al.; "Liver X receptors as integrators of metabolic and inflammatory signaling"; The Journal of Clinical Investigation, vol. 116, No. 3, Mar. 2006, pp. 607-614.
Joseph, Sean B. et al.; "Reciprocal regulation of inflammation and lipid metabolism by liver X receptors": Nature Medicine, vol. 9, No. 2 Feb. 2003, pp. 213-219.
Geyeregger, R. et al.; "Liver X receptors in cardiovascular and metabolic disease"; Cell. Mol. Life Sci., vol. 63, 2006, pp. 524-539.
Peet, Daniel J. et al.; "Cholesterol and Bile Acid Metabolism Are Impaired in Mice Lacking the Nuclear Oxysterol Receptor LXRα" Cell, vol. 93, May 29, 1998, pp. 693-704.
Alberti, S. et al.; "Hepatic cholesterol metabolism and resistance to dietary cholesterol in LXRβ-deficient mice"; Journal of Clinical Investigation, Mar. 2001, vol. 107, No. 5, pp. 565-573.

(Continued)

*Primary Examiner* — Yong Chu
*Assistant Examiner* — Michael Barker
(74) *Attorney, Agent, or Firm* — Westerman, Hattori, Daniels & Adrian, LLP

(57) ABSTRACT

The object is to provide a novel LXRβ agonist that is useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease. The solving means is a 1,3-dihydroisobenzofuran derivative represented by the following general formula (1) or salt thereof, or their solvate.

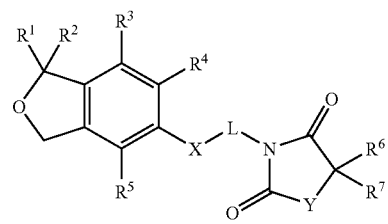

8 Claims, 2 Drawing Sheets

OTHER PUBLICATIONS

Tangirala, Rajendra K. et al.; "Identification of macrophage liver X receptors as inhibitors of atherosclerosis"; PNAS, vol. 99, No. 18, Sep. 3, 2002, pp. 11896-11901.

Terasaka, Naoki et al.; "T-0901317, a synthetic liver X receptor ligand, inhibits development of atherosclerosis in LDL receptor-deficient mice" FEBS Letters, vol. 536, 2003, pp. 6-11.

Cao, Guoqing et al.; "Antidiabetic Action of a Liver X Receptor Agonist Mediated by Inhibition of Hepatic Gluconeogenesis"; The Journal of Biological Chemistry, vol. 278, No. 2, Jan. 10, 2003 pp. 1131-1136.

Laffitte, Bryan A. et al.; "Activation of liver X receptor improvers glucose tolerance through coordinate regulation of glucose metabolism in liver and adipose tissue"; PNAS, vol. 100, No. 9, Apr. 29, 2003, pp. 5419-5424.

Lala, Deepak S.; "The Liver X receptors"; Current Opinion in Investigational Drugs, 2005, vol. 6, No. 9, 2005, pp. 934-943.

Groot, Pieter H. E. et al.; "Synthetic LXR agonists increase LDL in CETP species"; Journal of Lipid Research, vol. 46, 2005, pp. 2182-2191.

Schultz, Joshua R. et al.; "Role of LXRs in control of lipogenesis"; Genes & Development, vol. 14, 2000, pp. 2831-2838.

Lu, Timothy T. et al.; "Orphan Nuclear Receptors as eLiXiRs and FiXeRs of Sterol Metabolism"; The Journal of Biological Chemisry, vol. 276, No. 41, Oct. 12, 2001, pp. 37735-37738.

Auboeuf, Didier; "Tissue Distribution and Quantification of the Expression of mRNAs of Peroxisome Proliferator-Activated Receptors and Liver X Receptor α in Humans"; Diabetes, vol. 46, Aug. 1997, pp. 1319-1327.

Lund, Erik G. et al.; "Liver X Receptor Agonists as Potential Therapeutic Agents for Dyslipidemia and Atherosclerosis"; Arterioscler Thromb Vasc Biol., vol. 23, 2003, pp. 1169-1177.

Bradley, Michelle N. et al.; "LXR: A nuclear receptor target for cardiovascular disease?"; Drug Discovery Today: Therapeutic Strategies, 2005, pp. 97-103.

\* cited by examiner

1,3-DIHYDROISOBENZOFURAN DERIVATIVES

TECHNICAL FIELD

The present invention relates to a 1,3-dihydroisobenzofuran derivative which is a novel LXRβ agonist useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

BACKGROUND ART

Liver X receptor (LXR) is a nuclear receptor that was cloned as an orphan receptor whose ligand and function were both unknown. Subsequent study reported that some oxysterols including 22-(R)-hydroxycholesterol act as a ligand for LXR (non-patent documents 1 to 3). LXR, together with retinoid X receptor (RXR) which is another nuclear receptor, forms a heterodimer, to ligand-dependently control the transcription of a target gene.

As mammal LXR sub-types, two types of LXR genes (α and β) are known to exist. LXRα and LXRβ recognize the same sequence on a DNA and activate the transcription of a neighboring target gene. However, the expression-distributions of the two genes differ greatly. LXRα is specifically expressed on cholesterol metabolism-related tissues such as the liver, small intestines, or adipose tissues, whereas LXRβ is expressed ubiquitously on almost all tissues that have been examined (non-patent documents 4 and 5).

Many of the group of genes identified as target genes of LXRs are genes (ApoE, CETP, and LPL) related to a reverse cholesterol transport (RCT), including ABC transporters (ABCA1, ABCG1, ABCG5, and ABCG8). Therefore, it is expected that the activation of LXRs elevates the expression of these genes and activates reverse cholesterol transport pathways, thereby increases cholesterol efflux from the periphery and then increases HDL cholesterols and also lowers cholesterol content at an arteriosclerosis-affected region (non-patent document 6).

Further, LXRs are reported to play an important role via NF-κB suppression, in the expression control of inflammatory mediators such as NO-synthase, cyclooxygenase-2 (COX-2), and interleukin-6 (IL-6) (non-patent document 7). It is well known that the inflammation is very important at an arteriosclerosis-affected region, and it is expected that LXR ligands or LXR agonists will prevent arteriosclerosis exacerbation due to the expression of macrophage-inflammatory mediators at the affected region (non-patent documents 6 and 8).

Further, LXRα- and LXRβ-deficient mice fed on high-cholesterol diet have been reported to show symptoms such as fatty liver and elevated LDL-cholesterol level as well as reduced HDL-cholesterol level in the blood as compared to the case of normal mice fed on high-cholesterol diet (non-patent documents 9 and 10). More specifically, it is strongly suggested that LXRs play an important role in cholesterol metabolism. Moreover, by analyzing the symptoms of arteriosclerosis mouse models having normal LXRα and LXRβ functions in the liver, small intestines and the like but lacking LXRα and LXRβ in macrophages, it has been revealed that LXRα and LXRβ activities in macrophages strongly affect the incidence of arteriosclerosis (non-patent document 11). Therefore, the activation of reverse cholesterol transport through the LXR activation especially in macrophages is considered to be important for the treatment of arteriosclerosis.

As for the applications, LXR regulators or LXR agonists disclosed in the prior art documents are reported to have been applied to diseases such as hypercholesterolemia and atherosclerosis (patent documents 1 and 2). Further, LDL-receptor-deficient mice loaded with high-fat food, and administered with LXR ligand, have been reported to show an elevated HDL cholesterol level, lowered VLDL and LDL cholesterol levels, and reduced area of arteriosclerosis-affected region (non-patent document 12).

Further, LXR ligands or LXR agonists are expected to control sugar metabolism in the liver and adipose tissues, and thus to improve diabetes (non-patent documents 6 and 8). Recently, it has been reported that an administration of LXR agonist improved insulin sensitivity and blood glucose level in diabetes animal models (non-patent documents 13 and 14). Moreover, it is indicated as a potential therapeutic drug for Alzheimer's disease, inflammatory diseases, or skin diseases (non-patent document 15).

LXR agonists, however, are reported to increase LDL cholesterol in animal species having cholesteryl ester transfer proteins (CETP) (non-patent document 16). Further, in animal experiments, it has been observed that LXR activation in the liver by the LXR agonist administration enhances fatty-acid and triglyceride syntheses through the transcriptional activation of enzymes that are important for fatty-acid synthesis, for example, fatty-acid synthase (FAS) or stearyl-CoA fatty-acid desaturase (SCD-1) (non-patent document 17). Meanwhile, nothing is disclosed in the prior art documents on LXR α/β selectivity in relation to the disclosed LXR regulators, LXR ligands, LXR agonists and the like.

Therefore, there have been demands for an ideal synthetic LXR-binding compound without a dyslipidemia-exacerbating effect which acts through an elevated fatty-acid and triglyceride syntheses, while maintaining the agonist activity for reverse cholesterol transport activation by ABC transporters and for increased cholesterol-efflux from macrophages. As one approach to solve the problem, a compound that selectively activates LXRβs is considered to have an ideal profile that is expected to suppress the activation of LXRα highly expressed on the liver, as compared to the LXR regulators disclosed in the prior art documents, and to suppress the concerned side-effects of fatty-acid and triglyceride synthesis elevations (non-patent documents 6, 8, 15, 18, and 19). However, because ligand-binding sites of LXRα and LXRβ are highly homologous, it is considered that the creation of a compound that acts differently on LXRα and LXRβ is not easy.

In fact, compounds having an LXR-agonist effect have been reported, such as a benzofuran-5-acetic acid derivative (patent document 3), 2-aminoquinazoline-4-one derivative (patent document 4), tetrahydroquinoline derivative (patent document 5), tetrahydrocarbazol derivative (patent document 6), isoquinoline derivative (patent document 7), and naphthalene derivative (patent document 8), GW3965 that is an aromatic aminoalcohol derivative (Example 16 described in patent document 9), and T0901317 that is a benzenesulfonamide derivative (Example 12 described in patent document 10), but no agonist with high LXRβ selectivity has been reported to date and therefore an LXRβ selective compound has been awaited.

[Patent Document 1] Published Japanese translation of PCT international publication No. 2002-539155

[Patent Document 2] Published Japanese translation of PCT international publication No. 2004-509161

[Patent Document 3] WO2003/82192
[Patent Document 4] WO2004/24161
[Patent Document 5] WO2004/72046
[Patent Document 6] U.S Patent publication No. 2005/215577
[Patent Document 7] WO2004/58717
[Patent Document 8] WO2005/23188
[Patent Document 9] WO2002/24632
[Patent Document 10] WO2000/54759
[Non-patent Document 1] Janowski et al., *Nature*, 383, pp. 728-731, 1996
[Non-patent Document 2] Lehmann et al., J. Biol. Chem., 272, pp. 3137-3140, 1997
[Non-patent Document 3] Fu et al., J. Biol. Chem., 276, pp. 38378-38387, 2001
[Non-patent Document 4] Auboeuf et al., Diabetes, 46, pp. 1319-1327, 1997
[Non-patent Document 5] Lu et al., J. Biol. Chem., 276, pp. 37735-37738, 2001
[Non-patent Document 6] Zelcer et al., J. Clin. Invest., 116, pp. 607-614, 2006
[Non-patent Document 7] Joseph et al., Nat. Med., 9, pp. 213-219, 2003
[Non-patent Document 8] Geyeregger et al., Cell. Mol. Life Sci. 63, pp. 524-539, 2006
[Non-patent Document 9] Peet et al., Cell, 93, pp. 693-704, 1998
[Non-patent Document 10] Alberti et al., J. Clin. Invest., 107, pp. 565-573, 2001
[Non-patent Document 11] Tangirala et al., Proc. Natl. Acad. Sci. USA, 99, pp. 11896-11901, 2002
[Non-patent Document 12] Terasaka et al., FEBS Lett., 536, pp. 6-11, 2003
[Non-patent Document 13] Cao et al., J. Biol. Chem., 278, pp. 1131-1136, 2003
[Non-patent Document 14] Laffitte et al., Proc. Natl. Acad. Sci. USA, 100, pp. 5419-5424, 2003
[Non-patent Document 15] Lala et al., Curr. Opin. Investig. Drugs, 6, pp. 934-943, 2005
[Non-patent Document 16] Groot et al., *J. Lipid Res.*, 46, pp. 2182-2191, 2005
[Non-patent Document 17] Schultz et al., Genes Dev., 14, pp. 2831-2838, 2000
[Non-patent Document 18] Lund et al., *Arterioscler. Thromb. Vasc. Biol.*, 23, pp. 1169-1177, 2003
[Non-patent Document 19] Bradley et al., Drug Discov. Today Ther. Strateg. 2, pp. 97-103, 2005

BRIEF DESCRIPTION OF THE DRAWINGS

FIG. 1 is a table.

DISCLOSURE OF THE INVENTION

Figure 2:
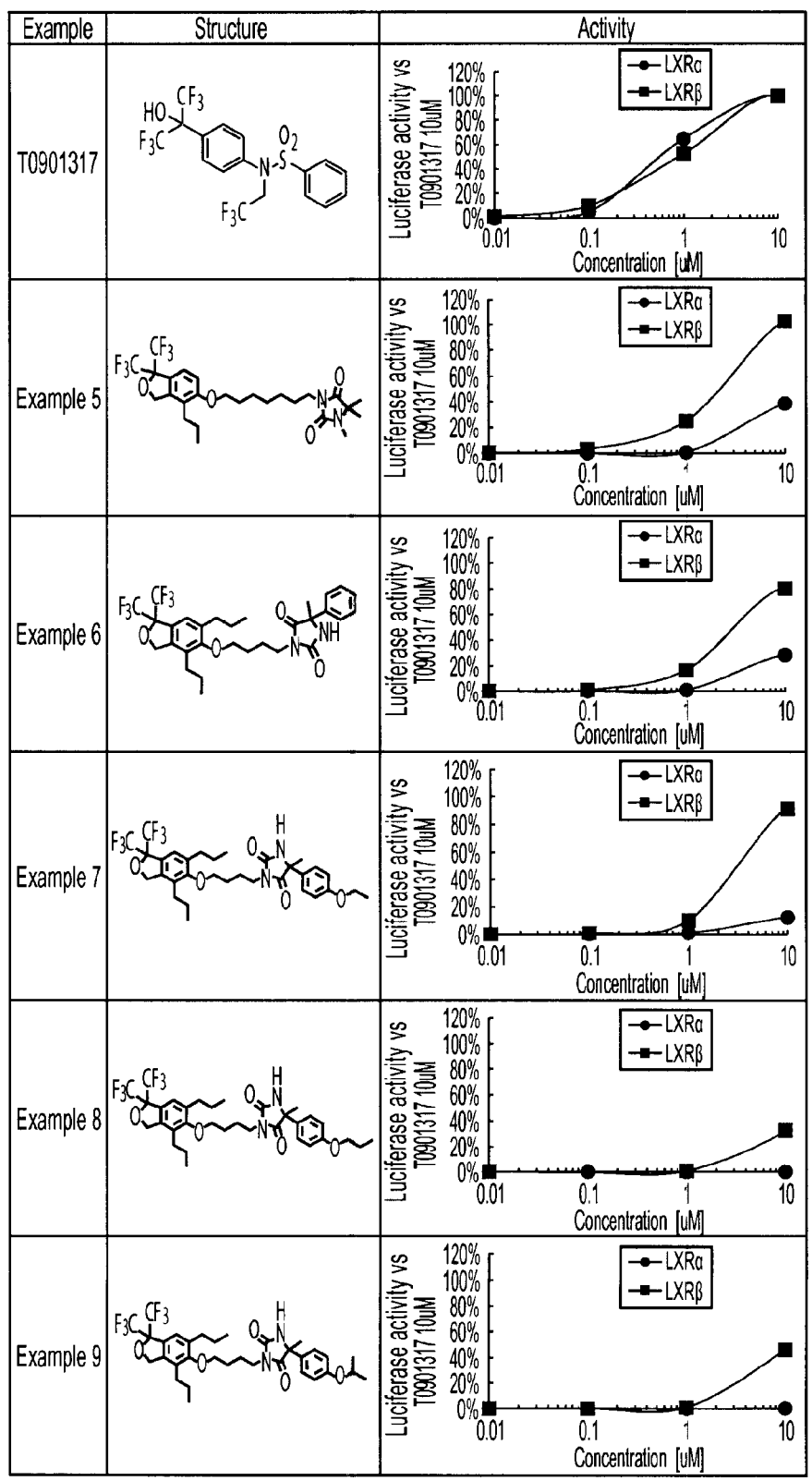
FIG. 2 is a table.

Problem to be Solved by the Invention

Thus, the object of the present invention is to prepare a novel compound that exhibits an agonist activity with high LXRβ selectivity.

Means to Solve the Problem

The present inventors made a keen study to achieve the above object and consequently, found that a 1,3-dihydroisobenzofuran derivative represented by general formula (I) described hereinbelow is an agonist with high LXRβ selectivity, and thus completed the present invention.

More specifically, the present invention relates to
[1] a 1,3-dihydroisobenzofuran derivative represented by the following general formula (1) or salt thereof, or their solvate:

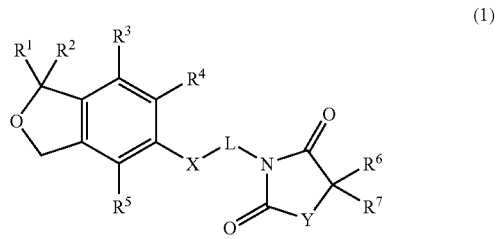

(wherein $R^1$ and $R^2$ are either same or different and represent a $C_{1-8}$ alkyl group or halo $C_{1-8}$ alkyl group; $R^3$, $R^4$, and $R^5$ are either same or different and represent a hydrogen atom, halogen atom, $C_{1-8}$ alkyl group, halo $C_{1-8}$ alkyl group, $C_{2-8}$ alkenyl group, $C_{2-8}$ alkynyl group, $C_{1-8}$ alkoxy group, $C_{1-8}$ acyl group, nitro group, cyano group, carboxyl group, carbamoyl group, or $C_{6-10}$ aryl $C_{1-8}$ alkyl group, wherein the $C_{6-10}$ aryl may have 1 to 3 substituents selected from the following group A; $R^6$ and $R^7$ are either same or different and represent a hydrogen atom, $C_{1-8}$ alkyl group, $C_{3-8}$ cycloalkyl group, halo $C_{1-8}$ alkyl group, $C_{6-10}$ aryl group or 5- to 11-membered heterocyclic group, wherein the $C_{6-10}$ aryl group and 5- to 11-membered heterocyclic group may have 1 to 3 substituents selected from the following group A, and $R^6$ and $R^7$ may together form a $C_{3-8}$ alkyl ring; L represents a $C_{2-10}$ alkyl chain, $C_{2-10}$ alkenyl chain, or $C_{2-6}$ alkyl-O—$C_{2-6}$ alkyl chain; X represents a —O— or —N($R^8$)—; $R^8$ represents a hydrogen atom or $C_{1-8}$ alkyl group; Y represents an O, S, —CH($R^9$)—, —CH$_2$CH($R^{10}$)—, —CH$_2$O—, or —N($R^{11}$)—; $R^9$ and $R^{10}$ are either same or different and represent a hydrogen atom or $C_{1-8}$ alkyl group; $R^{11}$ represents a hydrogen atom, $C_{1-8}$ alkyl group that may be substituted with a $C_{1-8}$ alkoxycarbonyl group, halo $C_{1-8}$ alkyl group, $C_{6-10}$ aryl group, or 5- to 11-membered heterocyclic group, wherein the $C_{6-10}$ aryl group and 5- to 11-membered heterocyclic group may have 1 to 3 substituents selected from the following group A),

[Group A: halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, $C_{1-8}$ alkoxy group, halo $C_{1-8}$ alkoxy group, $C_{1-8}$ acyl group, nitro group, amino group, mono $C_{1-6}$ alkylamino group, di $C_{1-6}$ alkylamino group, cyano group, hydroxy group, carboxyl group, $C_{1-8}$ alkoxycarbonyl group, carbamoyl group, $C_{6-10}$ aryl group, 5- to 11-membered heterocyclic group, $C_{1-6}$ alkylthio group, $C_{1-6}$ alkylsulfonyl group, $C_{6-10}$ arylthio group, $C_{6-10}$ arylsulfonyl group, tetrahydropyranyloxy group, and $C_{1-6}$ alkylenedioxy group];

[2] a medicine containing the 1,3-dihydroisobenzofuran derivative or salt thereof, or their solvate according to [1] as an active ingredient;

[3] the medicine according to [2], which is a preventative and/or therapeutic agent for atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease;

[4] an LXR regulator containing the 1,3-dihydroisobenzofuran derivative or salt thereof, or their solvate according to [1] as an active ingredient;

[5] a pharmaceutical composition consisting of the 1,3-dihydroisobenzofuran derivative or salt thereof, or their solvate according to [1] and a pharmaceutically acceptable carrier;

[6] a method for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease, which method comprises administering the 1,3-dihydroisobenzofuran derivative or salt thereof, or their solvate according to [1] to a patient in need of the treatment;

[7] use of the 1,3-dihydroisobenzofuran derivative or salt thereof, or their solvate according to [1] for a production of a formulation for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease.

Effect of the Invention

A 1,3-dihydroisobenzofuran derivative represented by general formula (1) of the present invention has an LXRβ agonist effect and is useful as a preventative and/or therapeutic agent for atherosclerosis, arteriosclerosis such as those resulting from diabetes; dyslipidemia; hypercholesterolemia; lipid-related diseases; inflammatory diseases caused by inflammatory cytokines, such as rheumatoid arthritis, osteoarthritis, allergic diseases, asthma, sepsis, psoriasis, and osteoporosis; autoimmune diseases such as systemic erythematosus, ulcerative colitis, and Crohn's disease; cardiovascular diseases such as ischemic cardiac disease and heart failure; cerebrovascular diseases; kidney diseases; diabetes; diabetes complications such as retinopathy, nephropathy, nerve disease, and coronary arterial disease; skin diseases such as allergic skin disease; obesity; nephritis; hepatitis; cancer; or Alzheimer's disease, and more preferably, as a preventative and/or therapeutic agent for atherosclerosis, arteriosclerosis such as those resulting from diabetes, dyslipidemia, hypercholesterolemia, lipid-related diseases, inflammatory diseases that are caused by inflammatory cytokines, skin diseases such as allergic skin diseases, diabetes, or Alzheimer's disease.

DETAILED DESCRIPTION OF THE INVENTION

The terms in the present invention are defined as follows.

In the present invention, examples of a "halogen" atom in the halogen atom, halo $C_{1-8}$ alkyl group, or halo $C_{1-8}$ alkoxy group include a fluorine atom, chlorine atom, bromine atom, and iodine atom.

In the present invention, a "$C_{1-8}$ alkyl group" means a straight-chained or branched-chained alkyl group with 1 to 8 carbons, and the examples include a methyl group, ethyl group, n-propyl group, isopropyl group, n-butyl group, isobutyl group, t-butyl group, n-pentyl group, isopentyl group, neopentyl group, 2-methylbutyl group, 2,2-dimethylpropyl group, n-hexyl group, isohexyl group, n-heptyl group, and n-octyl group.

In the present invention, a "halo $C_{1-8}$ alkyl group" means a group wherein preferably 1 to 9 halogen atoms are bound to a $C_{1-8}$ alkyl group, and the examples include trifluoromethyl group, 2-fluoroethyl group, 2-chloroethyl group, 2-bromoethyl group, 3-fluoropropyl group, 3-chloropropyl group, 4-fluorobutyl group, 4-chlorobutyl group, 2,2,2 trifluoroethyl group, 3,3,3-trifluoropropyl group, pentafluoroethyl group, and 2,2,2 trifluoro-l-trifluoromethylethyl group.

In the present invention, a "$C_{2-8}$ alkenyl group" means a straight-chained or branched-chained alkenyl group with 2 to 8 carbons, having a carbon-carbon double bond at any one or more sites on the alkyl chain. The examples include an ethenyl group, prop-1-en-1-yl group, prop-2-en-1-yl group, prop-1-en-2-yl group, but-1-en-1-yl group, but-2-en-1-yl group, but-3-en-1-yl group, but-1-en-2-yl group, but-3-en-2-yl group, pent-1-en-1-yl group, pent-4-en-1-yl group, pent-1-en-2-yl group, pent-4-en-2-yl group, 3-methyl-but-1-en-1-yl group, hex-1-en-1-yl group, hex-5-en-1-yl group, hept-1-en-1-yl group, hept-6-en-1-yl group, oct-1-en-1-yl group, and oct-7-en-1-yl group.

In the present invention, a "$C_{2-8}$ alkynyl group" means a straight-chained or branched-chained alkynyl group with 2 to 8 carbons, having a carbon-carbon triple bond at any one or more sites on the alkyl chain. The examples include an ethynyl group, prop-1-yn-1-yl group, prop-2-yn-1-yl group, but-1-yn-1-yl group, but-3-yn-1-yl group, 1-methyl-prop-2-yn-1-yl group, pent-1-yn-1-yl group, pent-4-yn-1-yl group, hex-1-yn-1-yl group, and hex-5-yn-1-yl group.

Specific examples of a "$C_{1-8}$ alkoxy group" in the present invention include a methoxy group, ethoxy group, n-propoxy group, isopropoxy group, n-butoxy group, isobutoxy group, sec-butoxy group, tert-butoxy group, n-pentoxy group, isopentoxy group, neopentoxy group, 1-methylbutoxy group, 1-ethylpropoxy group, n-hexyloxy group, isohexyloxy group, 4-methylpentoxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group, and 2-ethylbutoxy group.

In the present invention, a "halo $C_{1-8}$ alkoxy group" means a group wherein the aforementioned halo $C_{1-8}$ alkyl group is bound to an oxygen atom, and the examples include a trifluoromethoxy group, 2-fluoroethoxy group, 2-chloroethoxy group, 2-bromoethoxy group, 3-fluoropropoxy group, 3-chloropropoxy group, 4-fluorobutoxy group, 4-chlorobutoxy group, 2,2,2-trifluoroethoxy group, 3,3,3-trifluoropropoxy group, pentafluoroethoxy group, and 2,2,2-trifluoro-1-(trifluoromethyl)ethoxy group.

In the present invention, examples of a "$C_{1-8}$ acyl group" include a formyl group, acetyl group, propionyl group, butyryl group, isobutyryl group, valeryl group, isovaleryl group, pivaloyl group, acryloyl group, propioloyl group, methacryloyl group, benzoyl group, 2-naphthoyl group, 1-naphthoyl group, nicotinoyl group, isonicotinoyl group, 1-furoyl group, 2-furoyl group, and cinnamoyl group.

In the present invention, a "$C_{6-10}$ aryl $C_{1-8}$ alkyl group" means a group wherein the $C_{6-10}$ aryl group mentioned hereinbelow and the abovementioned $C_{1-8}$ alkyl group are bound. The examples include a benzyl group, phenethyl group, 3-phenyl-n-propyl group, 4-phenyl-n-butyl group, 5-phenyl-n-pentyl group, 8-phenyl-n-octyl group, and naphthylmethyl group.

In the present invention, a "$C_{3-8}$ cycloalkyl group," and a "$C_{3-8}$ cycloalkyl" in a $C_{3-8}$ cycloalkyl ring mean an alkyl group with 3 to 8 carbons having a cyclic moiety. The examples include a cyclopropyl group, cyclobutyl group, cyclopentyl group, cyclohexyl group, cycloheptyl group, cyclooctyl group, cyclopropylmethyl group, cyclohexylmethyl group, and preferably a "$C_{3-6}$ cycloalkyl group" with 3 to 6 carbons.

In the present invention, a "$C_{6-10}$ aryl group," and a "$C_{6-10}$ aryl" in a $C_{6-10}$ aryl $C_{1-8}$ alkyl group mean a monocyclic or polycyclic aryl group with 6 to 10 carbons wherein a polycyclic aryl group encompasses partially saturated groups in addition to fully unsaturated groups. The examples include a phenyl group, naphthyl group, azulenyl group, indenyl group, indanyl group, and tetralinyl group.

In the present invention, a "5- to 1'-membered heterocyclic group" means a 5- to 7-membered aromatic heterocycle, saturated heterocycle, unsaturated heterocycle or a condensed heterocycle made by a condensation of the above heterocycles and a benzene ring, wherein the above heterocycles contain 1 to 4 heteroatoms selected from a nitrogen atom, oxygen atom and sulfur atom in addition to a carbon atom as atoms constituting the ring. The examples include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrazin-3-yl group, pyrimidin-2-yl group, pyrimidin-4-yl group, pyrimidin-5-yl group, pyrimidin-6-yl group, pyridazin-3-yl group, pyridazin-4-yl group, 1,3-benzodioxol-4-yl group, 1,3-benzodioxol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, quinoxalin-2-yl group, quinoxalin-5-yl group, quinoxalin-6-yl group, indol-1-yl group, indol-2-yl group, indol-3-yl group, indol-4-yl group, indol-5-yl group, indol-6-yl group, indol-7-yl group, isoindol-1-yl group, isoindol-2-yl group, isoindol-4-yl group, isoindol-5-yl group, isoindol-6-yl group, isoindol-7-yl group, isobenzofuran-1-yl group, isobenzofuran-4-yl group, isobenzofuran-5-yl group, isobenzofuran-6-yl group, isobenzofuran-7-yl group, chromen-2-yl group, chromen-3-yl group, chromen-4-yl group, chromen-5-yl group, chromen-6-yl group, chromen-7-yl group, chromen-8-yl group, imidazol-1-yl group, imidazol-2-yl group, imidazol-4-yl group, imidazol-5-yl group, pyrazol-1-yl group, pyrazol-3-yl group, pyrazol-4-yl group, pyrazol-5-yl group, thiazol-2-yl group, thiazol-4-yl group, thiazol-5-yl group, oxazol-2-yl group, oxazol-4-yl group, oxazol-5-yl group, isoxazol-3-yl group, isoxazol-4-yl group, isoxazol-5-yl group, pyrrolidin-2-yl group, pyrrolidin-3-yl group, benzoimidazol-1-yl group, benzoimidazol-2-yl group, benzoimidazol-4-yl group, benzoimidazol-5-yl group, benzothiazole-2-yl group, benzothiazole-4-yl group, benzothiazol-5-yl group, benzoxazol-2-yl group, benzoxazol-4-yl group, benzoxazol-5-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group, isoquinolin-8-yl group, 1,3,4-thiadiazol-2-yl group, morpholino group, 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group, tetrazol-1-yl group, tetrazol-2-yl group, indolin-4-yl group, indolin-5-yl group, indolin-6-yl group, indolin-7-yl group, 1,2,3,4-tetrahydroquinolin-5-yl group, 1,2,3,4-tetrahydroquinolin-6-yl group, 1,2,3,4-tetrahydroquinolin-7-yl group, 1,2,3,4-tetrahydroquinolin-8-yl group, 1,2,3,4-tetrahydroisoquinolin-5-yl group, 1,2,3,4-tetrahydroisoquinolin-6-yl group, 1,2,3,4-tetrahydroisoquinolin-7-yl group, and 1,2,3,4-tetrahydroisoquinolin-8-yl group.

Specific examples of a "mono $C_{1-6}$ alkylamino group" of the present invention include a methylamino group, ethylamino group, n-propylamino group, isopropylamino group, n-butylamino group, sec-butylamino group, tert-butylamino group, n-pentylamino group, isopentylamino group, neopentylamino group, 1-methylbutylamino group, 1-ethylpropylamino group, n-hexylamino group, isohexylamino group, 4-methylpentylamino group, 3-methylpentylamino group, 2-methylpentylamino group, 1-methylpentylamino group, 3,3-dimethylbutylamino group, 2,2-dimethylbutylamino group, 1,1-dimethylbutylamino group, 1,2-dimethylbutylamino group, 1,3-dimethylbutylamino group, 2,3-dimethylbutylamino group, 1-ethylbutylamino group, and 2-ethylbutylamino group.

Specific examples of a "di $C_{1-6}$ alkylamino group" of the present invention include a dimethylamino group, methylethylamino group, diethylamino group, methyl-n-propylamino group, ethyl-n-propylamino group, di-n-propylamino group, methyl isopropylamino group, ethyl isopropylamino group, diisopropylamino group, methyl-n-butylamino group, ethyl-n-butylamino group, n-propyl-n-butylamino group, di-n-butylamino group, di-sec-butylamino group, di-tert-butylamino group, dipentylamino group, and dihexylamino group.

Specific examples of a "$C_{1-6}$ alkylthio group" of the present invention include a methylthio group, ethylthio group, n-propylthio group, isopropylthio group, n-butylthio group, isobutylthio group, sec-butylthio group, tert-butylthio group, n-pentylthio group, isopentylthio group, neopentylthio group, 1-methylbutylthio group, 1-ethylpropylthio group, n-hexylthio group, isohexylthio group, 4-methylpentylthio group, 3-methylpentylthio group, 2-methylpentylthio group, 1-methylpentylthio group, 3,3-dimethylbutylthio group, 2,2-dimethylbutylthio group, 1,1-dimethylbutylthio group, 1,2-dimethylbutylthio group, 1,3-dimethylbutylthio group, 2,3-dimethylbutylthio group, 1-ethylbutylthio group, and 2-ethylbutylthio group.

Specific examples of a "$C_{1-6}$ alkylsulfonyl group" of the present invention include a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, neopentylsulfonyl group, 1-methylbutylsulfonyl group, 1-ethylpropylsulfonyl group, n-hexylsulfonyl group, isohexylsulfonyl group, 4-methylpentylsulfonyl group, 3-methylpentylsulfonyl group, 2-methylpentylsulfonyl group, 1-methylpentylsulfonyl group, 3,3-dimethylbutylsulfonyl group, 2,2-dimethylbutylsulfonyl group, 1,1-dimethylbutylsulfonyl group, 1,2-dimethylbutylsulfonyl group, 1,3-dimethylbutylsulfonyl group, 2,3-dimethylbutylsulfonyl group, 1-ethylbutylsulfonyl group, and 2-ethylbutylsulfonyl group.

Specific examples of a "$C_{6-10}$ arylthio group" of the present invention include a phenylthio group, naphthylthio group, and azulenylthio group.

Specific examples of a "$C_{6-10}$ arylsulfonyl group" of the present invention include a benzenesulfonyl group, p-toluenesulfonyl group, p-chlorobenzenesulfonyl group, naphthalen-1-yl-sulfonyl group, and naphthalen-2-yl-sulfonyl group.

Specific examples of a "$C_{1-6}$ alkylenedioxy group" of the present invention include a methylenedioxy group, ethylenedioxy group, trimethylenedioxy group, tetramethylenedioxy group, pentamethylenedioxy group, and hexamethylenedioxy group.

Specific examples of a "$C_{1-8}$ alkoxycarbonyl group" of the present invention include a methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentoxycarbonyl group, isopentoxycarbonyl group, neopentoxycarbonyl group, 1-methylbutoxycarbonyl group, 1-ethylpropoxycarbonyl group, n-hexyloxycarbonyl group, isohexyloxycarbonyl group, 4-methylpentoxycarbonyl group, 3-methylpentoxycarbonyl group, 2-methylpentoxycarbonyl group, 1-methylpentoxycarbonyl group, 3,3-dimethylbutoxycarbonyl group, 2,2-dimethylbutoxycarbonyl group, 1,1-dimethylbutoxycarbonyl group, 1,2-dimethylbutoxycarbonyl group, 1,3-dimethylbutoxycarbonyl group, 2,3-dimethylbutoxycarbonyl group, 1-ethylbutoxycarbonyl group, and 2-ethylbutoxycarbonyl group.

In the present invention, a "$C_{2-10}$ alkyl chain" means a divalent hydrocarbon chain with 2 to 10 carbons having a straight-chain or a branch, and the examples include an ethylene chain, trimethylene chain, methylethylene chain, tetramethylene chain, 1,2-dimethylethylene chain, pentamethylene chain, 1-methyltetramethylene chain, 2-methyltetramethylene chain, hexamethylene chain, heptamethylene chain, octamethylene chain, nonamethylene chain, and decamethylene chain.

In the present invention, a "$C_{2-10}$ alkenyl chain" means a straight-chained or branched-chained divalent hydrocarbon chain with 2 to 10 carbons having a carbon-carbon double bond at any one or more sites on the above "$C_{2-10}$ alkyl chain," and the examples include a vinylene chain, propenylene chain, methylvinylene chain, butenylene chain (for example, 1-butenylene chain, 2-butenylene chain or the like), 1,2-dimethylvinylene chain, pentenylene chain, 1-methylbutenylene chain, 2-methylbutenylene chain, hexenylene chain, heptenylene chain, octenylene chain, nonenylene chain, decenylene chain, and isoplenylene chain.

In the present invention, a $C_{2-6}$ alkyl-O—$C_{2-6}$ alkyl chain means a chain wherein the above "$C_{2-6}$ alkyl chains" are bound via an oxygen atom. The examples include an ethylene-O-ethylene chain, ethylene-O-trimethylene chain, trimethylene-O-ethylene chain, and trimethylene-O-trimethylene chain.

Other groups that are not defined herein follow common definitions.

Followings are examples of the preferred modes of the present invention.

In general formula (I), the $C_{1-8}$ alkyl group of $R^1$ and $R^2$ is preferably a methyl group or ethyl group, and more preferably a methyl group.

In general formula (I), the halo $C_{1-8}$ alkyl group of $R^1$ and $R^2$ is preferably a 2,2,2-trifluoroethyl group or trifluoromethyl group and more preferably a trifluoromethyl group.

In general formula (I), $R^3$ is preferably a hydrogen atom.

In general formula (I), $R^4$ is preferably a hydrogen atom or $C_{1-8}$ alkyl group and more preferably a $C_{1-8}$ alkyl group.

In general formula (I), the $C_{1-8}$ alkyl group of $R^4$ is preferably an n-propyl group.

In general formula (I), $R^5$ is preferably a $C_{1-8}$ alkyl group.

In general formula (I), the $C_{1-8}$ alkyl group of $R^5$ is preferably a straight-chained $C_{1-8}$ alkyl group such as an ethyl group and n-propyl group and more preferably an n-propyl group.

In general formula (I), $R^6$ and $R^7$ are a hydrogen atom, $C_{1-8}$ alkyl group, halo $C_{1-8}$ alkyl group, $C_{3-8}$ cycloalkyl group, $C_{6-10}$ aryl group, or 5- to 11-membered heterocyclic group, and preferably a $C_{1-8}$ alkyl group or $C_{6-10}$ aryl group. It is more preferable that either or both of $R^6$ and $R^7$ are a $C_{1-8}$ alkyl group.

In general formula (I), the $C_{1-8}$ alkyl group of $R^6$ and $R^7$ is preferably a methyl group, ethyl group, n-propyl group, n-butyl group, or t-butyl group, and more preferably a methyl group.

In general formula (I), the halo $C_{1-8}$ alkyl group of $R^6$ and $R^7$ is preferably a trifluoromethyl group.

In general formula (I), the $C_{3-8}$ cycloalkyl group of $R^6$ and $R^7$ is preferably a cyclopropyl group or cyclobutyl group.

In general formula (I), the $C_{6-10}$ aryl group of $R^6$ and $R^7$ is preferably a phenyl group or naphthyl group. A substituent for the $C_{6-10}$ aryl group is preferably a "halogen atom" such as a fluorine atom, chlorine atom, and bromine atom; a "$C_{1-8}$ alkyl group" such as a methyl group, ethyl group, isopropyl group, t-butyl group, and sec-butyl group; a "halo $C_{1-8}$ alkyl group" such as a trifluoromethyl group; a "$C_{1-8}$ alkoxy group" such as a methoxy group, ethoxy group, n-propoxy group, isopropoxy group, and n-butoxy group; a "$C_{6-10}$ aryl group" such as a phenyl group; a "di $C_{1-6}$ alkylamino group" such as a dimethylamino group and diethylamino group; a "$C_{1-8}$ alkoxycarbonyl group" such as a t-butoxycarbonyl group; a "$C_{1-6}$ alkylenedioxy group" such as a methylenedioxy group and ethylenedioxy group; a nitro group, hydroxyl group, cyano group, carboxyl group, or tetrahydropyranyloxy group, and more preferably a "halogen atom" such as a fluorine atom and bromine atom; a "$C_{1-8}$ alkyl group" such as an ethyl group and isopropyl group; a "$C_{1-8}$ alkoxy group" such as a methoxy group and ethoxy group; or a "$C_{1-6}$ alkylenedioxy group" such as a methylenedioxy group and ethylenedioxy group.

In general formula (I), the 5- to 11-membered heterocyclic group of $R^6$ and $R^7$ is preferably a monocyclic 5- to 6-membered heterocyclic group such as a thienyl group, furyl group, and pyridyl group.

In general formula (1), a cyclopentyl ring is preferred when $R^6$ and $R^7$ together form a $C_{3-8}$ cycloalkyl ring.

In general formula (1), the "$C_{2-10}$ alkyl chain" of L is preferably a "$C_{2-6}$ alkyl chain" and more preferably a tetramethylene chain, pentamethylene chain, or hexamethylene chain.

In general formula (1), X is preferably a —O—.

In general formula (1), Y is preferably an O, S, —CH($R^9$)—, or —N($R^{11}$)—, and preferably a —N($R^{11}$)—.

In general formula (1), the "$C_{1-8}$ alkyl group" of $R^9$ is preferably a methyl group.

In general formula (1), $R^{11}$ is preferably a hydrogen atom or $C_{1-8}$ alkyl group that may be substituted with $C_{1-8}$ alkoxycarbonyl group.

In general formula (1), the "$C_{1-8}$ alkyl group that may be substituted with a $C_{1-8}$ alkoxycarbonyl group" of $R^{11}$ is preferably, for example, a methyl group, ethyl group, n-propyl group, isopropyl group, 2-methoxycarbonylethyl group, 3-methoxycarbonylpropan-1-yl group, or 4-methoxycarbonylbutan-1-yl group, and more preferably a methyl group.

Examples of an addition salt of a 1,3-dihydroisobenzofuran derivative represented by general formula (1) include alkali metal salts such as sodium salt and potassium salt; alkaline earth metal salts such as calcium salt and magnesium salt; organic base salts such as ammonium salt and trialkylamine salt; mineral acid salts such as hydrochloride salt and sulfate; and organic acid salts such as acetate, and there is no particular limitation as long as it is a pharmaceutically acceptable salt.

Examples of a solvate of a 1,3-dihydroisobenzofuran derivative represented by general formula (1) include a hydrate.

When there is a geometric isomer or optical isomer of a compound of the present invention, such isomers are included in the scope of the present invention.

Compound (I) can be produced by various known methods without particular limitation, and for example, can be produced according to the following reaction process.

More specifically, by reacting a dihydroisobenzofuran derivative shown by general formula (II) with a dihalide (III), a derivative shown by general formula (IV) is obtained. By reacting the obtained compound shown by general formula (IV) with an imide compound shown by general formula (V), a compound (I) can be produced. This reaction path shown by a chemical reaction formula is as follows:

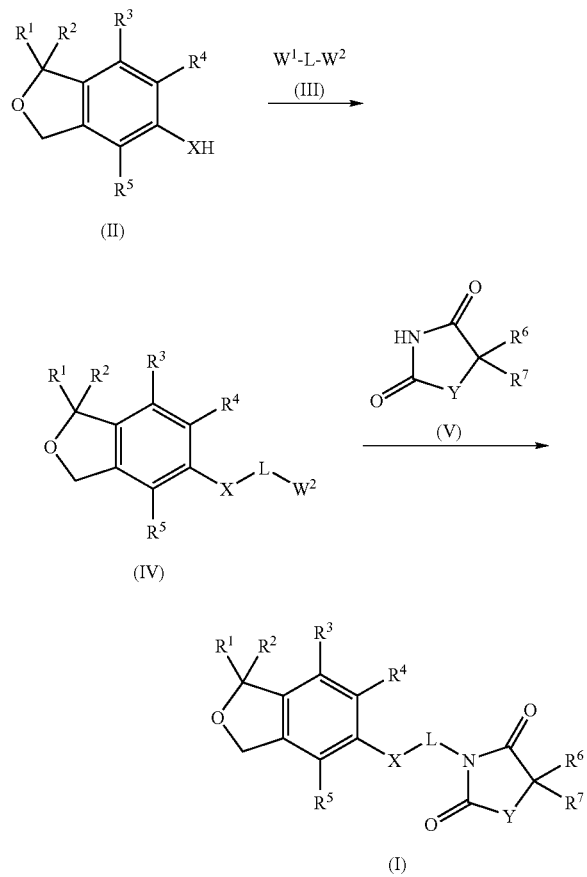

(wherein $R^1$ to $R^7$, X, and L have the same meaning as above and $W^1$ and $W^2$ show a halogen atom).

If an imide compound shown by general formula (V) has a reactive substituent, a compound of interest can be obtained by an addition of a protective group by a commonly used method (Protective Groups in Organic Synthesis Third Edition: John Wiley & Sons, Inc.; 1999) followed by a deprotection at an appropriate time.

By reacting a dihydroisobenzofuran derivative shown by general formula (II) with excessive amounts of dihalide (III) in a solvent in the presence or absence of a base, a derivative of general formula (IV) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water and the like. Further, a dihalide (III) can be used as a solvent. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; or lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium. A derivative of general formula (IV) which is a substance of interest can be obtained by conducting a reaction under the reaction conditions of −80 to 150° C., preferably of 0 to 100° C., for 1 minute to 5 days, preferably for 1 hour to 3 days.

By reacting the halide derivative (IV) obtained from the above reaction with an imide compound (V) in a solvent in the presence or absence of a base, a substance of interest (I) can be produced. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water and the like. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; or lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium. A substance of interest can be obtained by conducting a reaction under the reaction conditions of −80 to 150° C., preferably of 0 to 100° C., for 1 minute to 5 days, preferably for 1 hour to 3 days.

Further, a compound (I) can also be produced by reacting an imide compound shown by the above general formula (V) with a reagent shown by general formula (VI) to obtain an intermediate (VII), and then by further reacting with a dihydroisobenzofuran derivative (II). This reaction path shown by a chemical reaction formula is as follows:

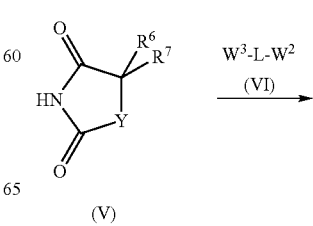

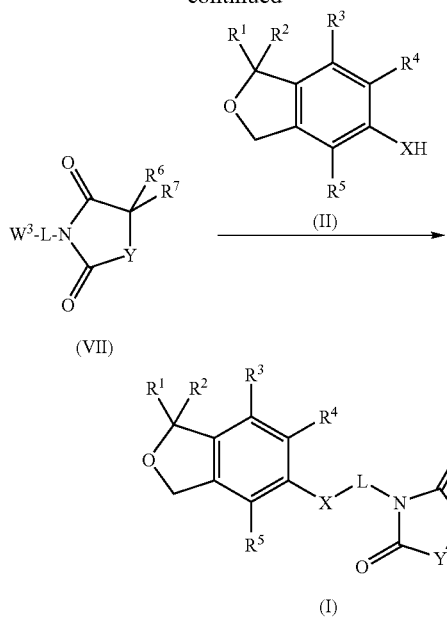

(wherein R¹ to R⁷, X, and L have the same meaning as above, W² shows a halogen atom, and W³ shows a halogen atom, aldehyde, aldehyde equivalent, or ketone).

The term an "aldehyde equivalent" refers to an aldehyde added with a protective group or to a substance that can be transformed into an aldehyde by a commonly used method (Comprehensive Organic Transformations Second Edition: John Wiley & Sons, Inc.; 1999). A commonly used method (Protective Groups in Organic Synthesis Third Edition: John Wiley & Sons, Inc.; 1999) can be used to add the protective group.

If an imide compound shown by general formula (V) has a reactive substituent, a compound of interest can be obtained by an addition of a protective group by a commonly used method (Protective Groups in Organic Synthesis Third Edition: John Wiley & Sons, Inc.; 1999), followed by a deprotection at an appropriate time.

By reacting an imide compound shown by general formula (V) with a reagent shown by general formula (VI) in a solvent in the presence or absence of a base, a derivative of general formula (VII) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water and the like. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; or lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium. A derivative of general formula (VII) which is a substance of interest can be obtained by conducting a reaction under the reaction conditions of −80 to 150° C., preferably of 0 to 100° C., for 1 minute to 5 days, preferably for 1 hour to 3 days.

When W³ is a halogen atom, a compound (I) can be produced by the same alkylation reaction as mentioned above.

Further, when X shows a —N(R⁸)—, a compound (I) can be produced using a reductive alkylation reaction with the use of a reagent shown by general formula (VII) in which W³ is an aldehyde group. A reductive alkylation reaction can be conducted by a commonly used method (Comprehensive Organic Transformations Second Edition: John Wiley & Sons, Inc.; 1999).

A dihydroisobenzofuran derivative can be produced by referring to a known method (J. Org. Chem., 32, pp 1479-1483, 1967., J. Med. Chem., 30, 178, 1987., Tetrahedron Lett., 37, pp 7395-7398, 1996) as a common production method.

More specifically, a dihydroisobenzofuran derivative shown by general formula (II) can be produced, for example, by referring to a known method (J. Org. Chem., 39, pp 2048-2050, 1974., WO97/08144). This reaction path shown by a chemical reaction formula is as follows:

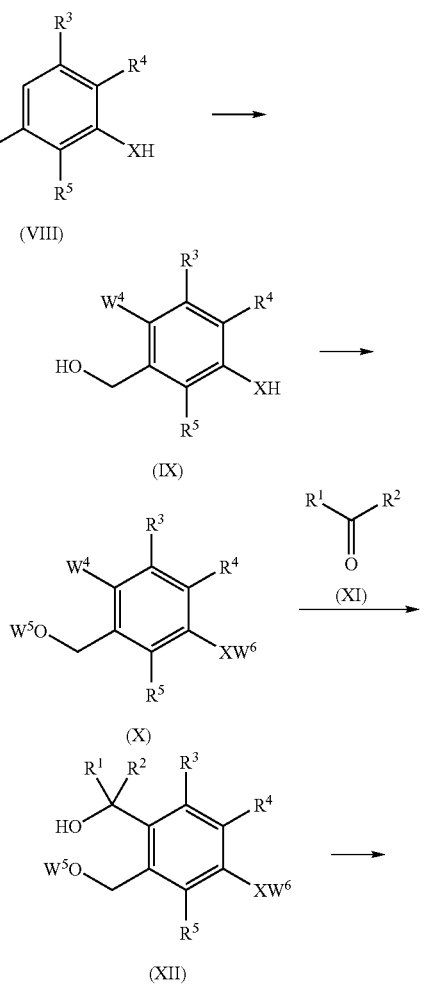

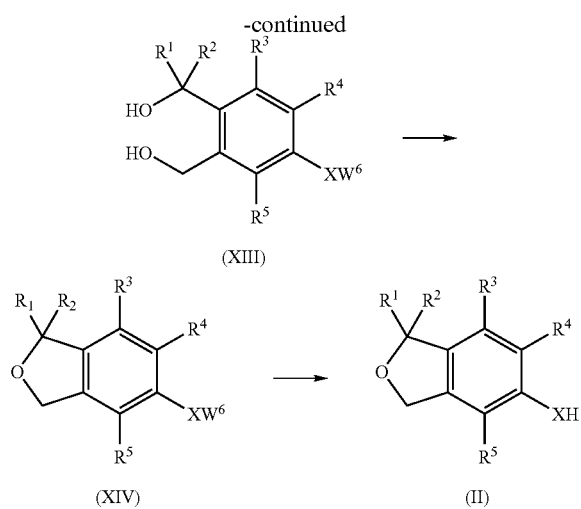

(wherein $R^1$ to $R^5$ and X have the same meaning as above, $W^4$ shows a halogen atom, and $W^5$ and $W^6$ show a protective group).

A derivative shown by general formula (VIII) can be produced, for example, by referring to a known method (Tetrahedron, 56(13), pp 1873-1882, 2000, WO99/12928).

By reacting a derivative shown by general formula (VIII) with a halogenating agent in a solvent in the presence or absence of a base, a derivative of general formula (IX) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, methanol, ethanol, isopropanol, dichloromethane, chloroform, water and the like. Further, a halide agent or base can be used as a solvent. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium; or organic base compounds such as pyridine and triethylamine. The halogenating agent is not particularly limited, and for example, chlorine, bromine, iodine, tetrabutylammonium tribromide, tetrabutylammonium triiodide, N-chlorosuccinimide, N-bromosuccinimide, N-iodosuccinimide, carbon tetrabromide or the like can be used. Further, a halide salt such as potassium bromide, potassium iodide, sodium bromide, and sodium iodide can be oxidized with an oxidant such as a hydrogen peroxide solution or an aqueous solution of sodium hypochlorite to produce a halogenating agent in the system, which is to be used in the reaction. A derivative of general formula (IX) which is a substance of interest can be obtained by conducting a reaction under the reaction conditions of −80 to 150° C., preferably of 0 to 100° C., for 1 minute to 5 days, preferably for 1 hour to 3 days.

A derivative shown by general formula (X) can be produced by adding a protective group to a derivative shown by general formula (IX) by a commonly used method (Protective Groups in Organic Synthesis Third Edition: John Wiley & Sons, Inc.; 1999). The compound of interest can be obtained by carrying out a deprotection at an appropriate time.

By reacting a derivative shown by general formula (X) with a base under an inert-gas atmosphere in a solvent and then with a carbonyl derivative shown by general formula (XI), a derivative of general formula (XII) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, and the like. The inert gas is not particularly limited, and for example, nitrogen, argon or the like can be used. The base is not particularly limited, and for example, organic metals or the like such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium can be used. A derivative of general formula (XII) which is a substance of interest can be obtained by conducting a reaction under the reaction conditions of −200 to 100° C., preferably of −80 to 10° C., for 1 minute to 5 days, preferably for 1 hour to 3 days.

A derivative shown by general formula (XII) can be converted to a derivative shown by general formula (XIII) by the deprotection of the protective group $W^5$ under deprotecting conditions referring to a commonly used method (Protective Groups in Organic Synthesis Third Edition: John Wiley & Sons, Inc.; 1999).

A derivative of general formula (XIV) which is a substance of interest can be obtained by subjecting a derivative shown by general formula (XIII) to the Mitsunobu reaction. The reaction can be carried out, for example, under an inert-gas atmosphere such as nitrogen and argon, in a solvent and in the presence of triphenylphosphine and diethyl azodicarboxylate. The solvent is not particularly limited, and for example, the followings can be used independently or in combination: tetrahydrofuran, toluene, dioxane, N,N-dimethylformamide, N-methylpyrrolidone, dimethylsulfoxide, and the like. A derivative of general formula (XIV) which is a substance of interest can be obtained by conducting a reaction under the reaction conditions of −80 to 150° C., preferably of −80 to 20° C., for 1 minute to 5 days, preferably for 1 hour to 3 days.

A derivative shown by general formula (XIV) can be converted to a derivative shown by general formula (II) by the deprotection of the protective group $W^6$ under deprotecting conditions referring to a commonly used method (Protective Groups in Organic Synthesis Third Edition: John Wiley & Sons, Inc; 1999).

Further, a derivative of general formula (XIV) can be obtained by reacting a derivative shown by general formula (XIII) with an acid. When $W^6$ is a substituent that is deprotected by an acid, a derivative of general formula (II) can be obtained. When $W^5$ is a substituent that is deprotected by an acid, a derivative of general formula (XII) may be reacted with the acid. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethylketone, methanol, ethanol, isopropanol, dichloromethane, chloroform, water and the like. Further, an acid can be used as a solvent. The acid is not particularly limited, and for example, mineral acids such as sulfuric acid, nitric acid, and hydrochloric acid or organic acids such as trifluoroacetic acid can be used. A derivative of general formula (IX) which is a substance of interest can be obtained by conducting a reaction under the reaction conditions of −80 to 150° C., preferably of 0 to 100° C., for 1 minute to 5 days, preferably for 1 hour to 3 days.

A 1,3-dihydroisobenzofuran derivative represented by general formula (I) of the present invention can be obtained by the above-mentioned methods, and optionally, further can be purified using an ordinary purifying method such as recrystallization method and column chromatography. Moreover, the above derivative can optionally be processed into an above-mentioned desired salt or solvate by a usual method.

So obtained 1,3-dihydroisobenzofuran derivative represented by general formula (I) or salt thereof, or their solvate (hereinafter, sometimes collectively described as "compounds represented by general formula (1)") shows a superior LXRβ agonist effect as shown in test examples described hereinbelow, and is useful as an active ingredient of a preventative and/or therapeutic agent for diseases of animal including humans, resulting from abnormal cholesterol metabolism, for example, atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

The pharmaceutical composition of the present invention contains a 1,3-dihydroisobenzofuran derivative represented by general formula (1) or salt thereof, or their solvate. The pharmaceutical composition may be used independently, but generally, is used by formulating with a pharmaceutically acceptable carrier, additive and the like. The administration form of the pharmaceutical composition is not particularly limited, and can be selected as desired according to the therapeutic purpose. For example, the administration form can be any of oral preparation, injection, suppository, ointment, inhalation, eye-drops, nasal preparation, adhesive patch and the like. The pharmaceutical composition suitable for these administration forms can be produced according to a known method of drug formulation.

When prepared into a solid oral formulation, a compound represented by general formula (1) can be added with an excipient and optionally, further with a binder, disintegrant, lubricant, coloring agent, flavoring agent, odor improving agent or the like, and then processed into a tablet, coated tablet, granules, powder, capsule or the like by a usual method. The additive may be those commonly used in this field. Examples of the excipient include lactose, sucrose, sodium chloride, glucose, starch, calcium carbonate, Kaolin, microcrystalline cellulose, and silicate. Examples of the binder include water, ethanol, propanol, simple syrup, dextrose solution, starch solution, gelatin solution, carboxymethylcellulose, hydroxypropylcellulose, hydroxypropylstarch, methylcellulose, ethylcellulose, shellack, calcium phosphate, and polyvinylpyrrolidone. Examples of the disintegrant include dry starch, sodium alginate, powdered agar, sodium hydrogen carbonate, calcium carbonate, sodium lauryl sulfate, monoglyceride stearate, and lactose. Examples of the lubricant include purified talc, stearate, borax, and polyethyleneglycol. Examples of the flavoring agent include sucrose, orange peel, citric acid, and tartaric acid.

When prepared into a liquid oral formulation, a compound represented by general formula (1) can be added with a flavoring agent, buffer, stabilizer, odor improving agent or the like, and then processed into an internal liquid formulation, syrup, elixir or the like. The flavoring agent may be those mentioned above, and examples of the buffer include sodium citrate, and examples of the stabilizer include tragacanth, gum Arabic, and gelatin.

When prepared into an injection, a compound represented by general formula (1) can be added with a pH adjuster, buffer, stabilizer, isotonic agent, local anesthetic or the like, and then processed into subcutaneous, intramuscular, and intravenous injections by a usual method. Examples of the pH adjuster and buffer include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the isotonic agent include sodium chloride and glucose.

When prepared into a suppository, a compound represented by general formula (1) can be added with a known carrier for suppository, for example, with polyethyleneglycol, lanolin, cacao butter, or fatty acid triglyceride, and optionally, further with a surfactant such as Tween®, and then processed into a suppository by a usual method.

When prepared into an ointment, a compound represented by general formula (1) can be formulated optionally with a commonly used base, stabilizer, moisturizer, preservative or the like, and then mixed and formulated by a usual method. Examples of the base include liquid paraffin, white petrolatum, white beeswax, octyldodecyl alcohol, and paraffin. Examples of the preservative include methyl p-hydroxybenzoate, ethyl p-hydroxybenzoate, and propyl p-hydroxybenzoate.

In addition to the above, an inhalation, eye-drops, or nasal preparation can be produced by a usual method.

The dose of a compound represented by general formula (I) varies depending on the age, weight, symptom, administration form, the number of doses and the like, but generally, it is preferable to administer a 1,3-dihydroisobenzofuran derivative represented by general formula (1) to an adult in an amount of 1 to 1000 mg per day as a single or several separate doses either orally or parenterally.

The present invention will be described further with reference to the following examples, while the scope of the present invention will not be limited to these examples.

Example 1

Preparation of 5-(benzo[d][1,3]dioxol-5-yl)-5-methyl-3-[4-[4-propyl-1,1-bis(trifluoromethyl)-1,3-dihydroisobenzofuran-5-yloxy]butyl]imidazolidine-2,4-dione a) Preparation of 3-(hydroxymethyl)-2-propylphenol

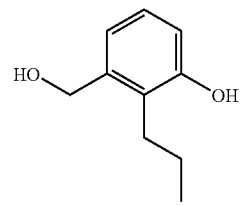

To a solution of 3-hydroxy-2-methyl propylbenzoate (Bioorg. Med. Chem., 6, pp 595-604, 1998, Japanese Laid-Open Patent Publication No. H10-087489) (1.50 g, 7.72 mmol) in tetrahydrofuran (50 mL), lithium aluminum hydride (645 mg, 17.0 mmol) was added at 0° C. The mixture was stirred at room temperature for 3 hours. The reaction solution was added with water and extracted with ethyl acetate. Subsequently, the organic layer was washed with saturated saline, dried using anhydrous sodium sulfate, and concentrated in vacuum. The obtained residue was purified using silica-gel column chromatography (hexane/ethyl acetate) and the title compound (1.17 g, 91%) was obtained as colorless crystalline powder.

$^1$H-NMR (CDCl$_3$) δ: 0.98 (3H, t, J=7.6 Hz), 1.48-1.63 (2H, m), 2.60-2.67 (2H, m), 4.60 (2H, s), 4.89 (2H, s), 6.70 (1H, dd, J=1.3, 7.9 Hz), 6.86 (1H, dd, J=1.3, 7.5 Hz), 6.96 (1H, dd, J=7.5, 7.9 Hz).

b) Preparation of 4-bromo-3-(hydroxymethyl)-2-propylphenol

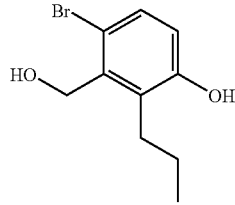

To a solution of 3-(hydroxymethyl)-2-propylphenol (1.05 g, 6.32 mmol) in dichloromethane (50 mL)-methanol (30 mL) mixtures, tetrabutylammonium tribromide (3.20 g, 6.64 mmol) was added at 0° C. The mixture was stirred at the same temperature for 1 hour. Solvent was evaporated under reduced pressure. The residue was added with water and extracted with ethyl acetate. Subsequently, the organic layer was washed with saturated saline, dried using anhydrous sodium sulfate, and concentrated in vacuum. The obtained residue was purified using silica-gel column chromatography (hexane/ethyl acetate) and the title compound (1.04 g, 67%) was obtained as colorless crystalline powder.

$^1$H-NMR (CDCl$_3$) δ: 0.99 (3H, t, J=7.5 Hz), 1.48-1.62 (2H, m), 2.66-2.80 (2H, m), 3.30 (1H, s), 4.75 (2H, s), 6.63 (1H, d, J=8.7 Hz), 7.20 (1H, d, J=8.7 Hz).

c) Preparation of 4-bromo-2-propyl-3-[(tetrahydro-2H-pyran-2-yloxy)methyl]phenol

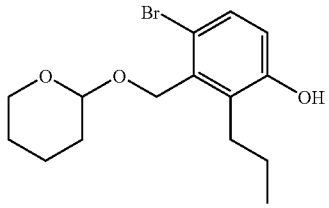

To a solution of 4-bromo-3-(hydroxymethyl)-2-propylphenol (1.04 g, 4.24 mmol) in dichloromethane (50 mL), p-toluenesulfonic acid-hydrate (81 mg, 0.424 mmol) and 3,4-dihydro-2H-pyrane (535 mg, 6.36 mmol) were added at room temperature. The mixture was stirred at same temperature for 5 hours. The reaction solution was added with water and extracted with chloroform. Subsequently, the organic layer was washed with saturated saline, dried using anhydrous sodium sulfate, and concentrated in vacuum. The residue was purified by silica-gel column chromatography (hexane/ethyl acetate) and the title compound (972 mg, 70%) was obtained as colorless oil.

$^1$H-NMR (CDCl$_3$) δ: 0.99 (3H, t, J=7.4 Hz), 1.45-1.85 (8H, m), 2.62-2.80 (2H, m), 3.58-3.70 (1H, m), 3.96-4.08 (1H, m), 4.57 (1H, d, J=10.5 Hz), 4.84 (1H, t, J=3.2 Hz), 4.95 (1H, d, J=10.5 Hz), 6.59 (1H, d, J=8.6 Hz), 7.25 (1H, d, J=8.6 Hz).

d) Preparation of 2-(6-bromo-3-(methoxymethoxy)-2-propylbenzyloxy)tetrahydro-2H-pyrane

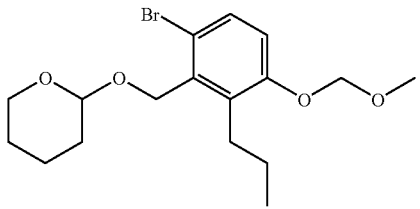

To a solution of 4-bromo-2-propyl-3-[(tetrahydro-2H-pyran-2-yloxy)methyl]phenol (972 mg, 2.95 mmol) in N,N-dimethylformamide (5 mL), sodium hydride (55% in oil, 257 mg, 5.90 mmol) and chloromethyl methyl ether (475 mg, 5.90 mmol) were added at 0° C. The mixture was stirred at room temperature for 2 hours. The reaction solution was added with water and extracted with ethyl acetate. Subsequently, the organic layer was washed with saturated saline, dried using anhydrous sodium sulfate, and concentrated under vacuum. The residue was purified by silica-gel column chromatography (hexane/ethyl acetate), and the title compound (910 mg, 83%) was obtained as colorless oil.

$^1$H-NMR (CDCl$_3$) δ: 0.98 (3H, t, J=7.3 Hz), 1.46-1.88 (8H, m), 2.83 (2H, dt, J=2.0, 7.6 Hz), 3.46 (3H, s), 3.62 (1H, dtd, J=1.3, 4.3, 11.2 Hz), 4.01 (1H, dt, J=3.3, 11.2 Hz), 4.58 (1H, d, J=10.9 Hz), 4.82 (1H, t, J=3.3 Hz), 4.97 (1H, d, J=10.9 Hz), 5.18 (2H, s), 6.94 (1H, d, J=8.9 Hz), 7.36 (1H, d, J=8.9 Hz).

e) Preparation of 1,1,1,3,3,3-hexafluoro-2-[4-(methoxymethoxy)-3-propyl-2-[(tetrahydro-2H-pyran-2-yloxy)methyl]phenyl]propan-2-ol

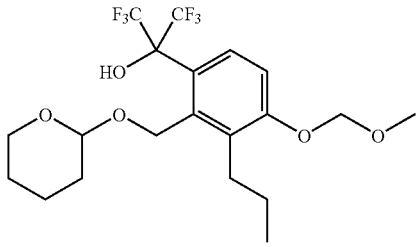

Under an argon atmosphere, n-butyl lithium (1.58 mol/L hexane solution 1.55 mL, 2.45 mmol) was dropped at −78° C. into a solution of 2-(6-bromo-3-(methoxymethoxy)-2-propylbenzyloxy)tetrahydro-2H-pyrane (725 mg, 1.75 mmol) in tetrahydrofuran (8 mL). The mixture was stirred at the same temperature for 15 minutes and then stirred at the elevated temperature of −45° C. for 1.5 hours. A tetrahydrofuran (4 mL) solution of hexafluoroacetone was dropped at −78° C., and the mixture was stirred at 0° C. for 5 hours and then stirred at room temperature for 12 hours. The reaction solution was added with water and extracted with ethyl acetate. Subsequently, the organic layer was washed with saturated saline, dried using anhydrous sodium sulfate, and concentrated in vacuum. The residue was purified by silica-gel column chromatography (hexane/ethyl acetate), and the title compound (728 mg, 90%) was obtained as colorless oil.

$^1$H-NMR (CDCl$_3$) δ: 0.99 (3H, t, J=7.4 Hz), 1.45-1.86 (8H, m), 2.73-2.82 (2H, m), 3.53 (3H, s), 3.59-3.66 (1H, m), 3.97-4.02 (1H, m), 4.66 (1H, d, J=10.5 Hz), 4.75-4.81 (4H, m), 6.67 (1H, d, J=8.5 Hz), 7.19 (1H, d, J=8.5 Hz), 7.46 (1H, s).

f) Preparation of 1,1,1,3,3,3-hexafluoro-2-[2-(hydroxymethyl)-4-(methoxymethoxy)-3-propylphenyl]propan-2-ol

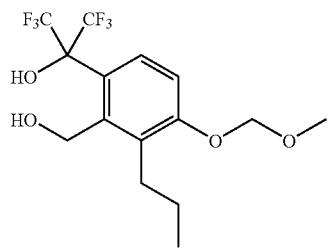

To a solution of 1,1,1,3,3,3-hexafluoro-2-[4-(methoxymethoxy)-3-propyl-2-[(tetrahydro-2H-pyran-2-yloxy)methyl]phenyl]propan-2-ol (883.2 mg, 1.92 mmol) in tetrahydrofuran (10 mL), water (5 mL), and acetic acid (20 mL) were added, and the mixture was stirred at 50° C. for 3 hours. The reaction solution was neutralized with an aqueous solution of sodium hydrogen carbonate and then extracted with ethyl acetate. The organic layer was washed with saturated saline, dried using anhydrous sodium sulfate, and concentrated under vacuum. The obtained residue was purified by silica-gel column chromatography (hexane/ethyl acetate), and the title compound (678 mg, 92%) was obtained as colorless oil.

$^1$H-NMR (CDCl$_3$) δ: 1.00 (3H, t, J=7.3 Hz), 1.47-1.57 (2H, m), 2.73-2.80 (2H, m), 3.54 (3H, s), 4.82 (2H, s), 4.88 (2H, s), 6.76 (1H, d, J=8.9 Hz), 7.31 (1H, d, J=8.9 Hz), 7.68 (1H, s), 7.75 (1H, s).

g) Preparation of 5-(methoxymethoxy)-4-propyl-1,1-bis(trifluoromethyl)-1,3-dihydroisobenzofuran

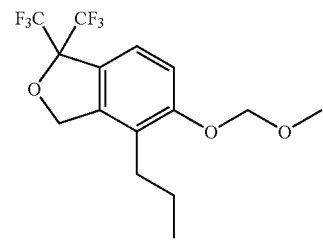

To a solution of 1,1,1,3,3,3-hexafluoro-2-[2-(hydroxymethyl)-4-(methoxymethoxy)-3-propylphenyl]propan-2-ol (1.29 g, 3.43 mmol) and triphenylphosphine (1.98 g, 7.55 mmol) in dichloromethane (15 mL), diethyl azodicarboxylate (2.2 mol/L toluene solution, 4.67 mL, 10.27 mmol) was added under ice-cold conditions and the mixture was stirred overnight. The reaction solution was added with water and extracted with ethyl acetate. Subsequently, the organic layer was washed with saturated saline, dried using anhydrous sodium sulfate, and concentrated in vacuum. The residue was purified by silica-gel column chromatography (hexane/ethyl acetate) and the title compound (1.14 g, 93%) was obtained as colorless oil.

$^1$H-NMR (CDCl$_3$) δ: 0.96 (3H, t, J=7.3 Hz), 1.60 (2H, sextet, J=7.3 Hz), 2.51 (2H, t, J=7.3 Hz), 3.55 (3H, s), 4.88 (2H, s), 5.31 (2H, s), 6.81 (1H, d, J=8.2 Hz), 7.20 (1H, d, J=8.2 Hz).

h) Preparation of 4-propyl-1,1-bis(trifluoromethyl)-1,3-dihydroisobenzofuran-5-ol

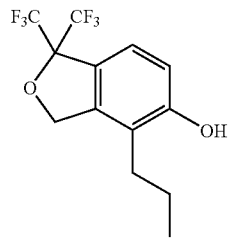

To 5-(methoxymethoxy)-4-propyl-1,1-bis(trifluoromethyl)-1,3-dihydroisobenzofuran (1.12 g, 3.13 mmol), hydrochloric acid-ethanol (2 mol/L, 5 mL) was added and the mixture was stirred at room temperature for 2 hours. The reaction solution was concentrated under vacuum. The obtained residue was purified by silica-gel column chromatography (hexane/ethyl acetate) and of the title compound (952.6 mg, 96%) was obtained as colorless crystalline powder.

$^1$H-NMR (CDCl$_3$) δ: 0.96 (3H, t, J=7.3 Hz), 1.61 (2H, sextet, J=7.3 Hz), 2.50 (2H, t, J=7.3 Hz), 5.02 (1H, s), 5.30 (2H, s), 6.80 (1H, d, J=7.9 Hz), 7.21 (1H, d, J=7.9 Hz).

i) Preparation of 5-(4-bromobutoxy)-4-propyl-1,1-bis(trifluoromethyl)-1,3-dihydroisobenzofuran

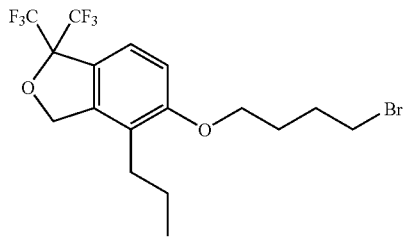

A N,N-Dimethylformamide (10 mL) solution of 4-propyl-1,1-bis(trifluoromethyl)-1,3-dihydroisobenzofuran-5-ol (800 mg, 2.55 mol), 1,4-dibromobutane (2.75 mL, 12.73 mmol) and potassium carbonate (528 mg, 3.82 mmol) was stirred at room temperature overnight. The reaction solution was added with water and extracted with ethyl acetate. Subsequently, the organic layer was washed with saturated saline, dried using anhydrous sodium sulfate, and concentrated in vacuum. The obtained residue was purified by silica-gel column chromatography (hexane:ethyl acetate=50:1) and the title compound (1.136 g, 99%) was obtained as colorless oil.

$^1$H-NMR (CDCl$_3$) δ: 0.93 (3H, t, J=7.4 Hz), 1.57 (2H, sextet, J=7.3 Hz), 1.97-2.14 (4H, m), 2.49 (2H, t, J=7.6 Hz), 3.51 (2H, t, J=6.3 Hz), 4.03 (2H, t, J=5.4 Hz), 5.30 (2H, s), 6.86 (1H, d, J=8.4 Hz), 7.29 (1H, d, J=8.1 Hz).

k) Preparation of 5-(benzo[d][1,3]dioxol-5-yl)-5-methyl-3-[4-[4-propyl-1,1-bis(trifluoromethyl)-1,3-dihydroisobenzofuran-5-yloxy]butyl]imidazolidine-2,4-dione:

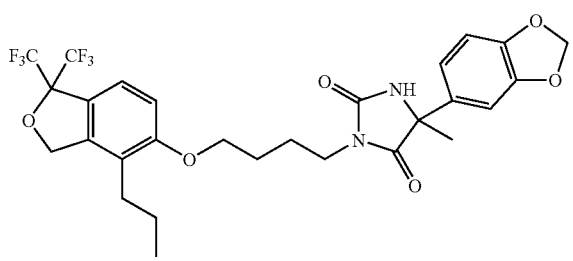

To a N,N-Dimethylformamide (2 mL) solution of 5-(4-bromobutoxy)-4-propyl-1,1-bis(trifluoromethyl)-1,3-dihydroisobenzofuran (25 mg, 0.0557 mmol), potassium carbonate mg, 0.111 mmol) and 5-(benzo[d][1,3]dioxol-5-yl)-5-methylimidazolidine-2,4-dione (CAS: 308122-40-9: DE335993) (19.6 mg, 0.0835 mmol) were added and the mixture was stirred overnight. The reaction solution was added with water and extracted with ethyl acetate. Subsequently, the organic layer was washed with saturated saline, dried using anhydrous sodium sulfate, and concentrated in vacuum. The residue was purified by thin-layer silica-gel column chromatography (hexane:ethyl acetate=2:1) and of the title compound (30.7 mg, 92%) was obtained as colorless oil.

$^1$H-NMR (CDCl$_3$) δ: 0.89 (3H, t, J=7.4 Hz), 1.46-1.59 (2H, m), 1.75-1.85 (7H, m), 2.45 (2H, t, J=7.4 Hz), 3.57-3.60 (2H, m), 3.99-4.00 (2H, m), 5.28 (2H, s), 5.96 (2H, s), 6.32 (1H, s), 6.77-6.84 (2H, m), 6.93-6.99 (2H, m), 7.26 (1H, d, J=5.4 Hz).

By the same method as Example 1, the following compounds were synthesized from a known compound or a compound that can be obtained by a known method.

| Example 2 | 5-(3-methoxyphenyl)-5-methyl-3-(4-(4-propyl-1,1-bis(trifluoromethyl)-1,3-dihydroisobenzofuran-5-yloxy)butyl)imidazolidine-2,4-dione |
|---|---|

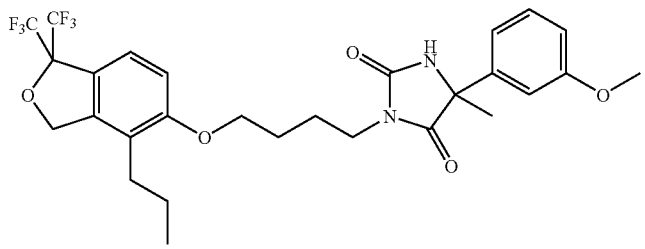

$^1$H-NMR (CDCl$_3$) δ: 0.88 (3H, t, J=7.4 Hz), 1.45-1.58 (2H, m), 1.75-1.88 (7H, m), 2.45 (2H, t, J=7.4 Hz), 3.60 (2H, t, J=6.3 Hz), 3.75 (3H, s), 3.98 (2H, t, J=5.3 Hz), 5.28 (2H, s), 6.07 (1H, s), 6.80-6.89 (2H, m), 7.05-7.08 (2H, m), 7.25-7.33 (2H, m).

| Example 3 | 5-(3-bromo-4-fluorophenyl)-5-methyl-3-(4-(4-propyl-1,1-bis(trifluoromethyl)-1,3-dihydroisobenzofuran-5-yloxy)butyl)imidazolidine-2,4-dione |
|---|---|

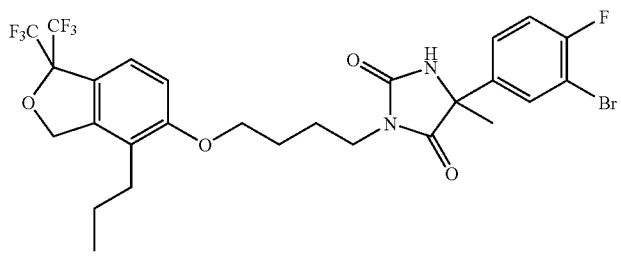

$^1$H-NMR (CDCl$_3$) δ: 0.88 (3H, t, J=7.3 Hz), 1.52 (2H, sextet, J=7.3 Hz), 1.72-1.90 (7H, m), 2.45 (2H, t, J=7.3 Hz), 3.61 (2H, t, J=6.5 Hz), 3.99 (2H, t, J=5.6 Hz), 5.28 (2H, s), 6.49 (1H, s), 6.83 (1H, d, J=8.5 Hz), 7.13 (1H, dd, J=8.3, 8.8 Hz), 7.26 (1H, d, J=8.5 Hz), 7.46 (1H, ddd, J=2.2, 4.4, 8.8 Hz), 7.72 (1H, dd, J=2.4, 6.3 Hz).

Example 4

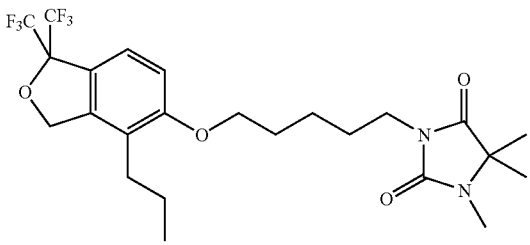

1,5,5-trimethyl-3-(5-(4-propyl-1,1-bis(trifluoromethyl)-1,3-dihydroisobenzofuran-5-yloxy)pentyl)imidazolidine-2,4-dione $^1$H-NMR (CDCl$_3$) δ: 0.92 (3H, t, J=7.2 Hz), 1.37 (6H, s), 1.44-1.90 (8H, m), 2.48 (2H, t, J=7.6 Hz), 2.89 (3H, s), 3.54 (2H, t, J=7.3 Hz), 3.98 (2H, t, J=6.2 Hz), 5.29 (2H, s), 6.85 (1H, d, J=8.6 Hz), 7.27 (1H, s, J=8.4 Hz).

Example 5

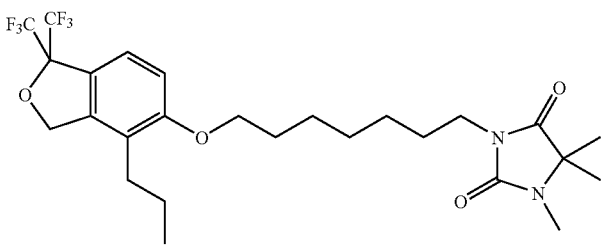

1,5,5-trimethyl-3-(7-(4-propyl-1,1-bis(trifluoromethyl)-1,3-dihydroisobenzofuran-5-yloxy)heptyl)imidazolidine-2,4-dione $^1$H-NMR (CDCl$_3$) δ: 0.92 (3H, t, J=7.3 Hz), 1.32-1.69 (16H, m), 1.75-1.85 (2H, m), 2.48 (2H, t, J=7.6 Hz), 2.88 (3H, s), 3.50 (2H, t, J=7.2 Hz), 3.97 (2H, t, J=6.2 Hz), 5.29 (2H, s), 6.85 (1H, d, J=8.6 Hz), 7.28 (1H, d, J=8.1 Hz).

Example 6

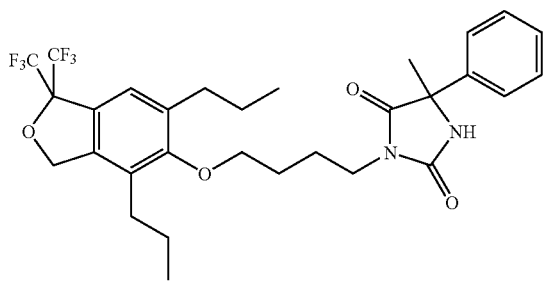

3-(4-(4,6-dipropyl-1,1-bis(trifluoromethyl)-1,3-dihydroisobenzofuran-5-yloxy)butyl)-5-methyl-5-phenylimidazolidine-2,4-dione $^1$H-NMR (CDCl$_3$) δ: 0.85-0.95 (6H, m), 1.48-1.68 (4H, m), 1.77-1.90 (7H, m), 2.44 (2H, t, J=7.8 Hz), 2.57 (2H, t, J=7.8 Hz), 3.62 (2H, t, J=6.9 Hz), 3.76 (2H, t, J=6.0 Hz), 5.25 (2H, s), 6.10 (1H, s), 7.14 (1H, s), 7.31-7.41 (3H, m), 7.48-7.51 (2H, m).

Example 7 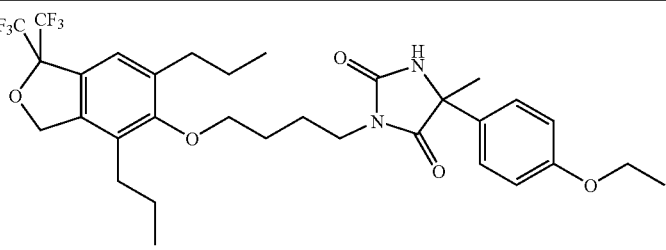 3-(4-(4,6-dipropyl-1,1-bis(trifluoromethyl)-1,3-dihydroisobenzofuran-5-yloxy)butyl)-5-(4-ethoxyphenyl)-5-methylimidazolidine-2,4-dione ¹H-NMR (CDCl₃) δ: 0.88-0.97 (6H, m), 1.40 (3H, t, J=6.9 Hz), 1.48-1.65 (4H, m), 1.74-1.85 (7H, m), 2.44 (2H, t, J=7.6 Hz), 2.57 (2H, t, J=7.6 Hz), 3.61 (2H, t, J=6.6 Hz), 3.76 (2H, t, J=5.6 Hz), 4.01 (2H, q, J=6.9 Hz), 5.25 (2H, s), 5.86 (1H, s), 6.88 (2H, d, J=8.9 Hz), 7.14 (1H, s), 7.37 (2H, d, J=8.9 Hz).

Example 8 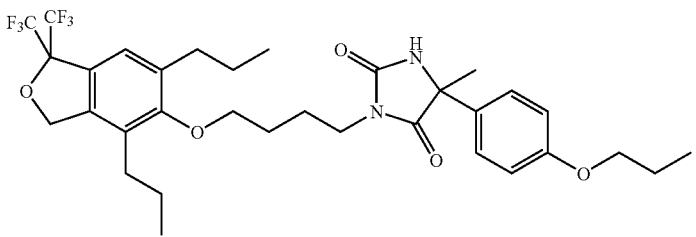 3-(4-(4,6-dipropyl-1,1-bis(trifluoromethyl)-1,3-dihydroisobenzofuran-5-yloxy)butyl)-5-methyl-5-(4-propoxyphenyl)imidazolidine-2,4-dione ¹H-NMR (CDCl₃) δ: 0.85-0.97 (6H, m), 1.02 (3H, t, J=7.6 Hz), 1.45-1.66 (6H, m), 1.70-1.85 (7H, m), 2.43 (2H, t, J=7.6 Hz), 2.56 (2H, t, J=7.6 Hz), 3.61 (2H, t, J=6.9 Hz), 3.76 (2H, t, J=5.6 Hz), 3.88 (2H, q, J=6.6 Hz), 5.25 (2H, s), 5.79 (1H, s), 6.88 (2H, d, J=8.9 Hz), 7.13 (1H, s), 7.37 (2H, d, J=8.9 Hz).

Example 9 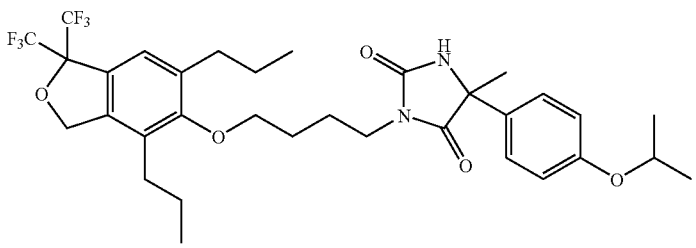 3-(4-(4,6-dipropyl-1,1-bis(trifluoromethyl)-1,3-dihydroisobenzofuran-5-yloxy)butyl)-5-(4-isopropoxyphenyl)-5-methylimidazolidine-2,4-dione ¹H-NMR (CDCl₃) δ: 0.88-0.97 (6H, m), 1.41 (6H, d, J=5.9 Hz), 1.48-1.66 (4H, m), 1.73-1.88 (7H, m), 2.44 (2H, t, J=7.6 Hz), (2H, t, J=7.6 Hz), 3.61 (2H, t, J=6.6 Hz), 3.76 (2H, t, J=5.6 Hz), 4.52 (1H, septet, J=5.9 Hz), 5.25 (2H, s), 5.76 (1H, s), 6.87 (2H, d, J=8.9 Hz), 7.14 (1H, s), 7.36 (2H, d, J=8.9 Hz).

By the same method as Example 1, the compounds listed on the following tables were synthesized from a known compound or a compound that can be obtained by a known method. The NMR data of a part of compounds are shown on Table 1-15.

TABLE 1-1

Example 10 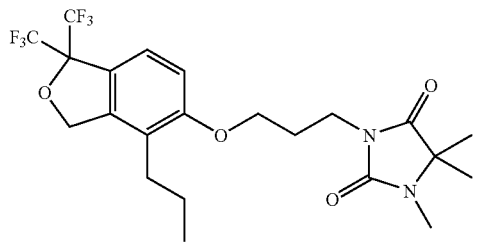 1,5,5-trimethyl-3-(3-(4-propyl-1,1-bis(trifluoromethyl)-1,3-dihydroisobenzofuran-5-yloxy)propyl)imidazolidine-2,4-dione Example 11 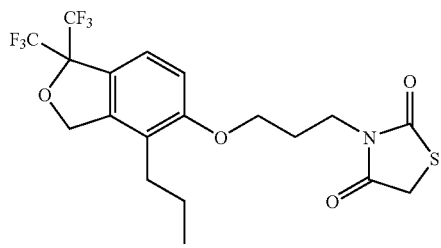 3-(3-(4-propyl-1,1-bis(trifluoromethyl)-1,3-dihydroisobenzofuran-5-yloxy)propyl)thiazolidine-2,4-dione Example 12 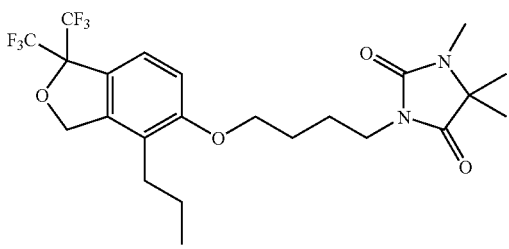 1,5,5-trimethyl-3-(4-(4-propyl-1,1-bis(trifluoromethyl)-1,3-dihydroisobenzofuran-5-yloxy)butyl)imidazolidine-2,4-dione Example 13 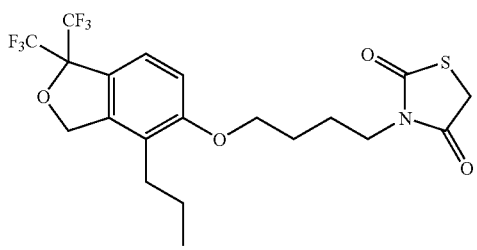 3-(4-(4-propyl-1,1-bis(trifluoromethyl)-1,3-dihydroisobenzofuran-5-yloxy)butyl)thiazolidine-2,4-dione Example 14 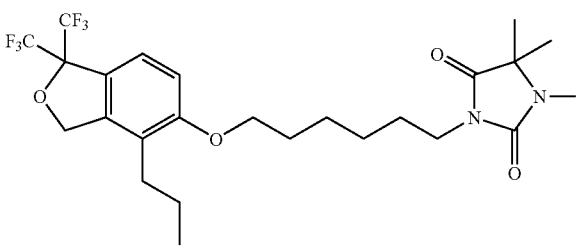 1,5,5-trimethyl-3-(6-(4-propyl-1,1-bis(trifluoromethyl)-1,3-dihydroisobenzofuran-5-yloxy)hexyl)imidazolidine-2,4-dione Example 15 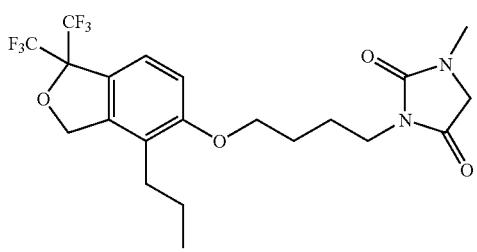 1-methyl-3-(4-(4-propyl-1,1-bis(trifluoromethyl)-1,3-dihydroisobenzofuran-5-yloxy)butyl)imidazolidine-2,4-dione TABLE 1-1-continued Example 16

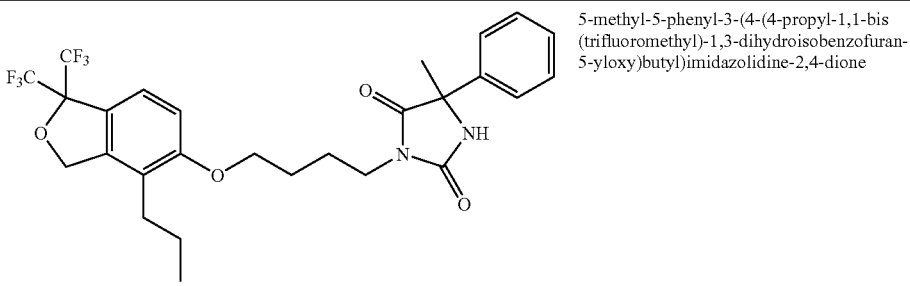

5-methyl-5-phenyl-3-(4-(4-propyl-1,1-bis(trifluoromethyl)-1,3-dihydroisobenzofuran-5-yloxy)butyl)imidazolidine-2,4-dione Example 17

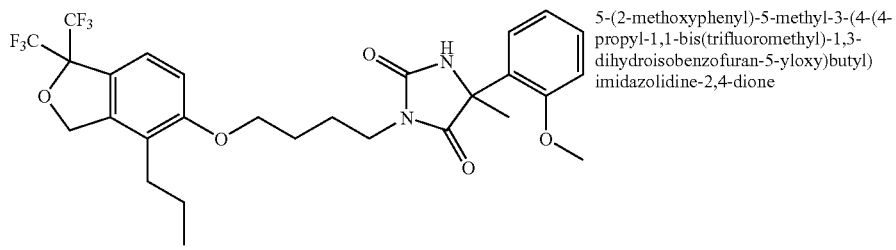

5-(2-methoxyphenyl)-5-methyl-3-(4-(4-propyl-1,1-bis(trifluoromethyl)-1,3-dihydroisobenzofuran-5-yloxy)butyl)imidazolidine-2,4-dione

TABLE 1-2

Example 18

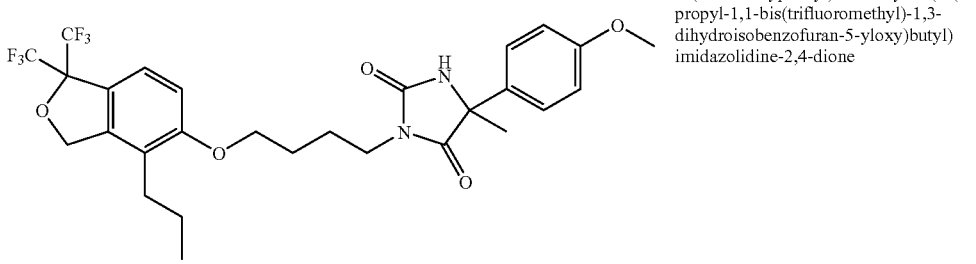

5-(4-methoxyphenyl)-5-methyl-3-(4-(4-propyl-1,1-bis(trifluoromethyl)-1,3-dihydroisobenzofuran-5-yloxy)butyl)imidazolidine-2,4-dione Example 19

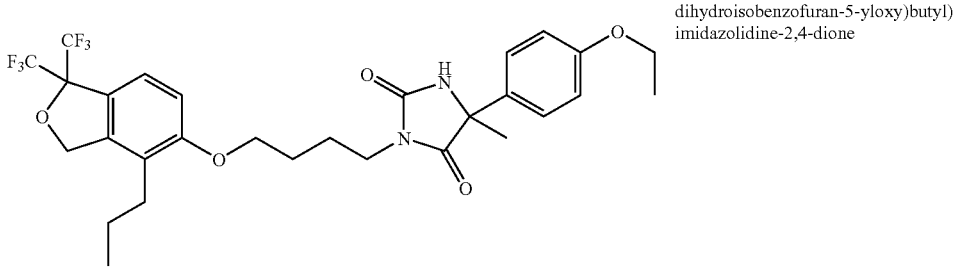

5-(4-ethoxyphenyl)-5-methyl-3-(4-(4-propyl-1,1-bis(trifluoromethyl)-1,3-dihydroisobenzofuran-5-yloxy)butyl)imidazolidine-2,4-dione Example 20

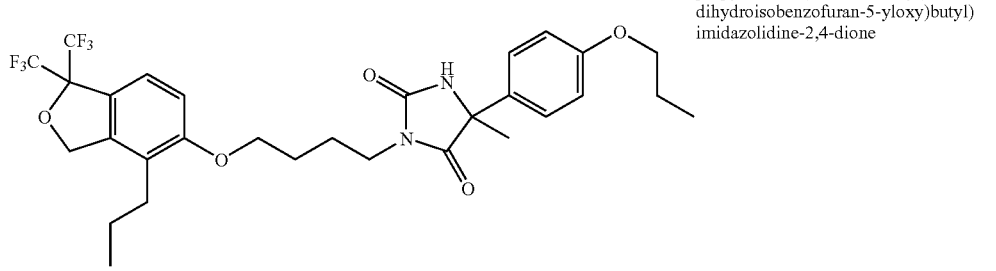

5-methyl-5-(4-propoxyphenyl)-3-(4-(4-propyl-1,1-bis(trifluoromethyl)-1,3-dihydroisobenzofuran-5-yloxy)butyl)imidazolidine-2,4-dione TABLE 1-2-continued Example 21
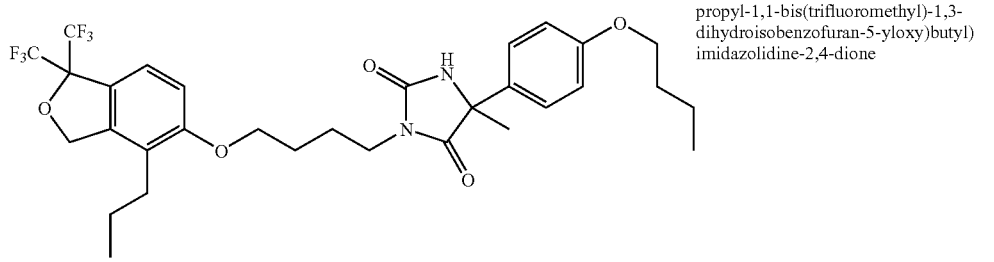
5-(4-butoxyphenyl)-5-methyl-3-(4-(4-propyl-1,1-bis(trifluoromethyl)-1,3-dihydroisobenzofuran-5-yloxy)butyl)imidazolidine-2,4-dione Example 22
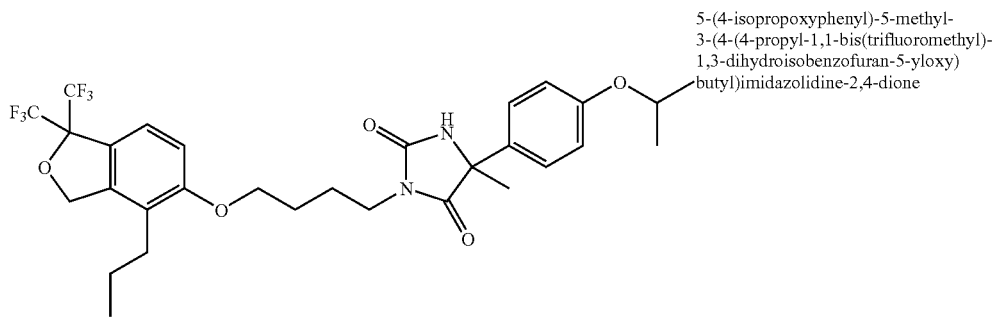
5-(4-isopropoxyphenyl)-5-methyl-3-(4-(4-propyl-1,1-bis(trifluoromethyl)-1,3-dihydroisobenzofuran-5-yloxy)butyl)imidazolidine-2,4-dione Example 23
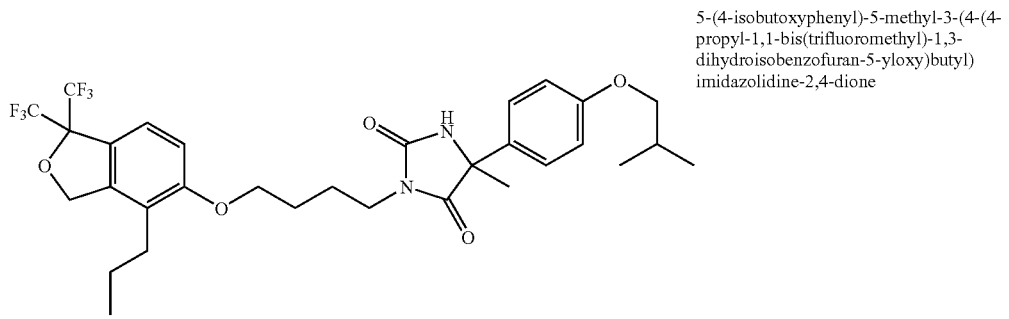
5-(4-isobutoxyphenyl)-5-methyl-3-(4-(4-propyl-1,1-bis(trifluoromethyl)-1,3-dihydroisobenzofuran-5-yloxy)butyl)imidazolidine-2,4-dione Example 24
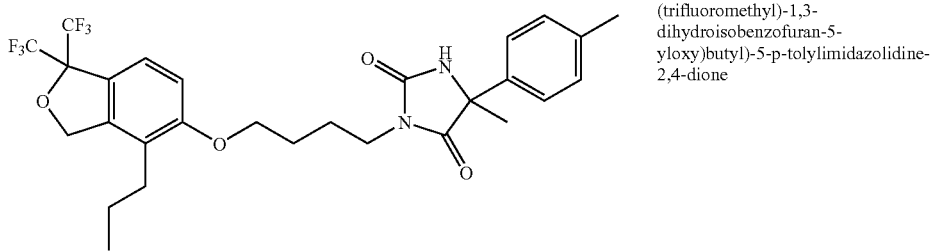
5-methyl-3-(4-(4-propyl-1,1-bis(trifluoromethyl)-1,3-dihydroisobenzofuran-5-yloxy)butyl)-5-p-tolylimidazolidine-2,4-dione Example 25
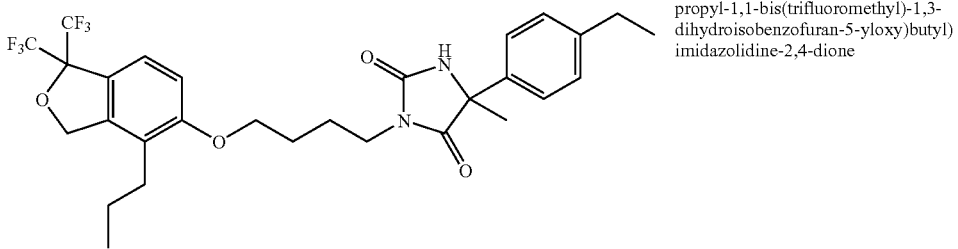
5-(4-ethylphenyl)-5-methyl-3-(4-(4-propyl-1,1-bis(trifluoromethyl)-1,3-dihydroisobenzofuran-5-yloxy)butyl)imidazolidine-2,4-dione

TABLE 1-3

| Example 26 | 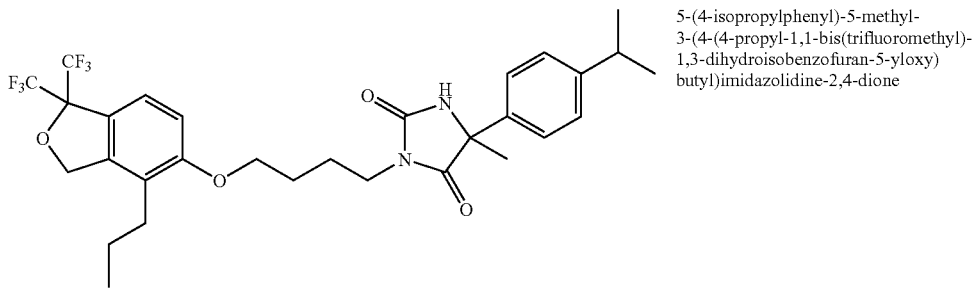 | 5-(4-isopropylphenyl)-5-methyl-3-(4-(4-propyl-1,1-bis(trifluoromethyl)-1,3-dihydroisobenzofuran-5-yloxy)butyl)imidazolidine-2,4-dione |
| --- | --- | --- |
| Example 27 | 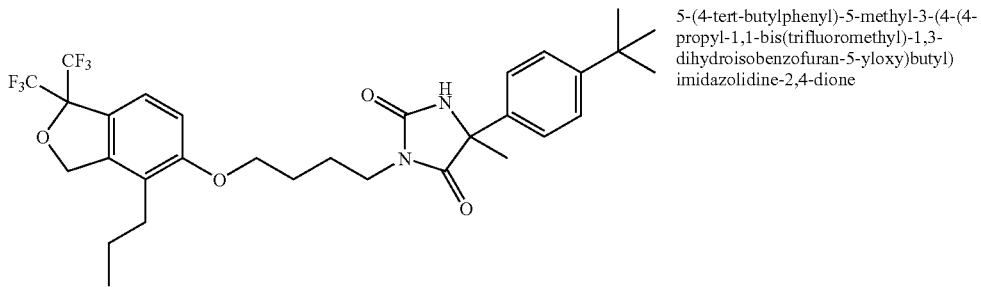 | 5-(4-tert-butylphenyl)-5-methyl-3-(4-(4-propyl-1,1-bis(trifluoromethyl)-1,3-dihydroisobenzofuran-5-yloxy)butyl)imidazolidine-2,4-dione |
| Example 28 | 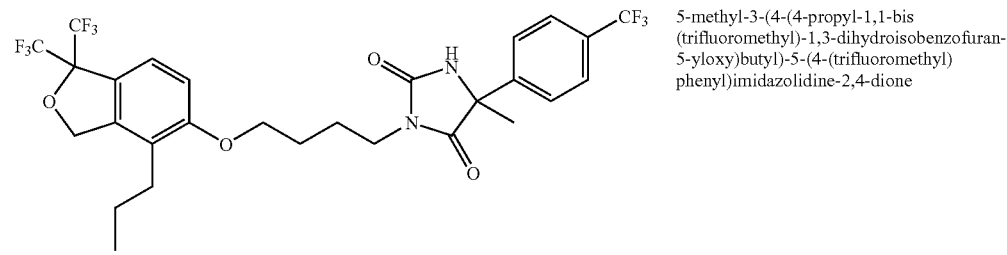 | 5-methyl-3-(4-(4-propyl-1,1-bis(trifluoromethyl)-1,3-dihydroisobenzofuran-5-yloxy)butyl)-5-(4-(trifluoromethyl)phenyl)imidazolidine-2,4-dione |
| Example 29 | 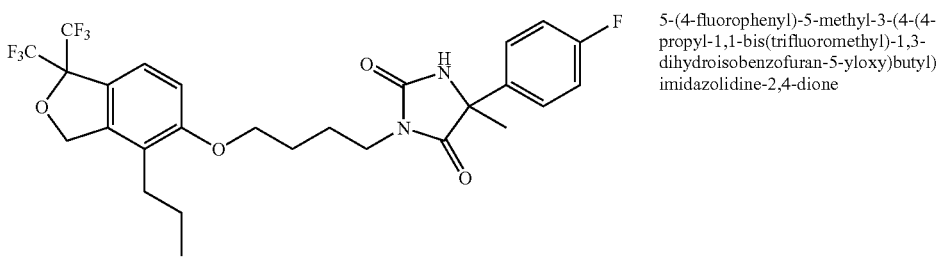 | 5-(4-fluorophenyl)-5-methyl-3-(4-(4-propyl-1,1-bis(trifluoromethyl)-1,3-dihydroisobenzofuran-5-yloxy)butyl)imidazolidine-2,4-dione |
| Example 30 | 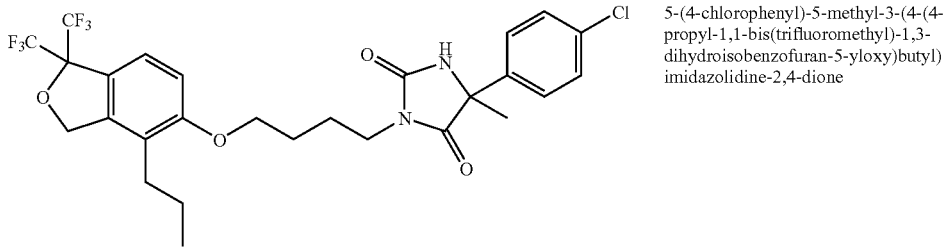 | 5-(4-chlorophenyl)-5-methyl-3-(4-(4-propyl-1,1-bis(trifluoromethyl)-1,3-dihydroisobenzofuran-5-yloxy)butyl)imidazolidine-2,4-dione |
| Example 31 | 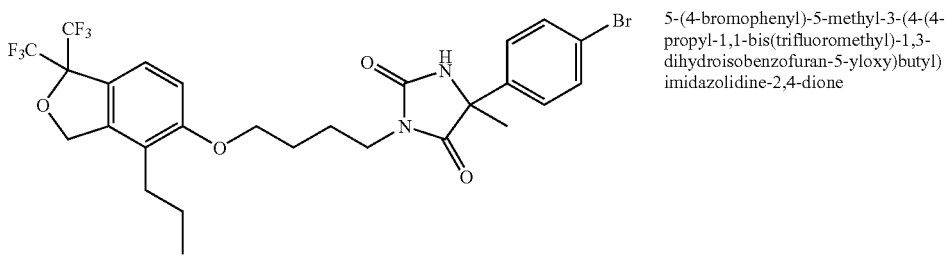 | 5-(4-bromophenyl)-5-methyl-3-(4-(4-propyl-1,1-bis(trifluoromethyl)-1,3-dihydroisobenzofuran-5-yloxy)butyl)imidazolidine-2,4-dione |

TABLE 1-3-continued

| Example 32 | 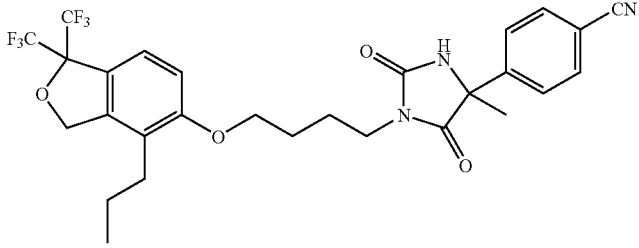 | 4-(4-methyl-2,5-dioxo-1-(4-(4-propyl-1,1-bis(trifluoromethyl)-1,3-dihydroisobenzofuran-5-yloxy)butyl)imidazolidine-4-yl)benzonitrile |
| Example 33 | 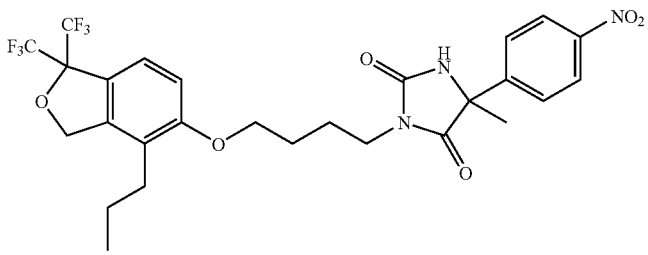 | 5-methyl-5-(4-nitrophenyl)-3-(4-(4-propyl-1,1-bis(trifluoromethyl)-1,3-dihydroisobenzofuran-5-yloxy)butyl)imidazolidine-2,4-dione |

TABLE 1-4

| Example 34 | 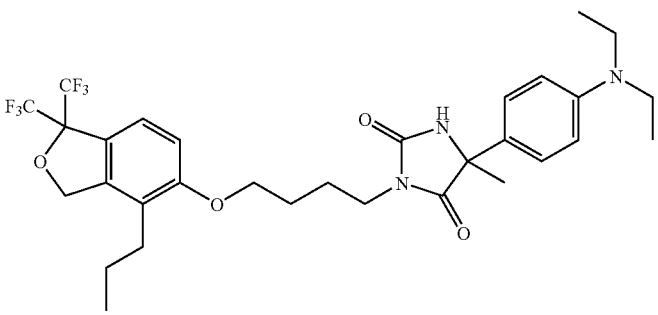 | 5-(4-(diethylamino)phenyl)-5-methyl-3-(4-(4-propyl-1,1-bis(trifluoromethyl)-1,3-dihydroisobenzofuran-5-yloxy)butyl)imidazolidine-2,4-dione |
| Example 35 | 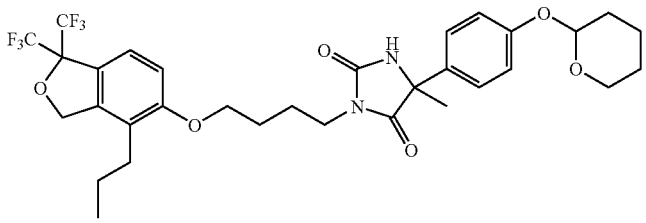 | 5-methyl-3-(4-(4-propyl-1,1-bis(trifluoromethyl)-1,3-dihydroisobenzofuran-5-yloxy)butyl)-5-(4-(tetrahydro-2H-pyran-2-yloxy)phenyl)imidazolidine-2,4-dione |
| Example 36 | 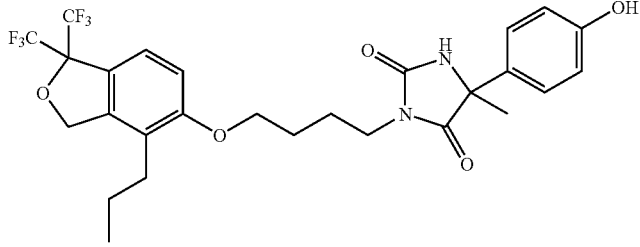 | 5-(4-hydroxyphenyl)-5-methyl-3-(4-(4-propyl-1,1-bis(trifluoromethyl)-1,3-dihydroisobenzofuran-5-yloxy)butyl)imidazolidine-2,4-dione |

TABLE 1-4-continued

| Example 37 | 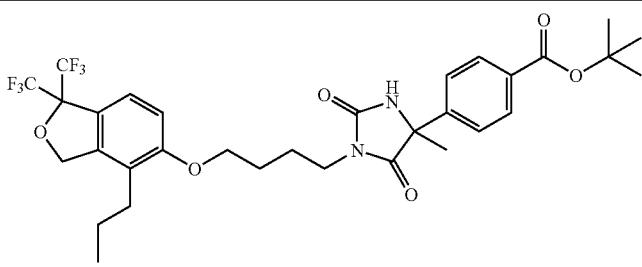 | tert-butyl 4-(4-methyl-2,5-dioxo-1-(4-(4-propyl-1,1-bis(trifluoromethyl)-1,3-dihydroisobenzofuran-5-yloxy)butyl)imidazolidin-4-yl)benzoate |
| --- | --- | --- |
| Example 38 | 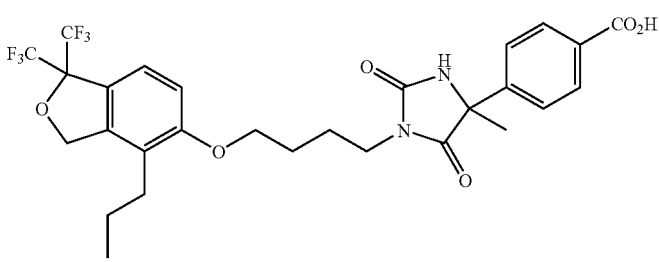 | 4-(4-methyl-2,5-dioxo-1-(4-(4-propyl-1,1-bis(trifluoromethyl)-1,3-dihydroisobenzofuran-5-yloxy)butyl)imidazolidin-4-yl)benzoic acid |
| Example 39 | 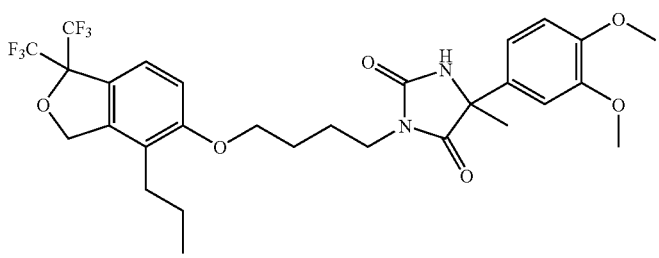 | 5-(3,4-dimethoxyphenyl)-5-methyl-3-(4-(4-propyl-1,1-bis(trifluoromethyl)-1,3-dihydroisobenzofuran-5-yloxy)butyl)imidazolidine-2,4-dione |
| Example 40 | 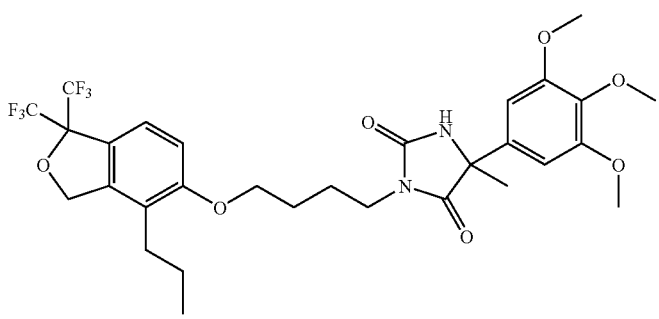 | 5-methyl-3-(4-(4-propyl-1,1-bis(trifluoromethyl)-1,3-dihydroisobenzofuran-5-yloxy)butyl)-5-(3,4,5-trimethoxyphenyl)imidazolidine-2,4-dione |

TABLE 1-5

| Example 41 | 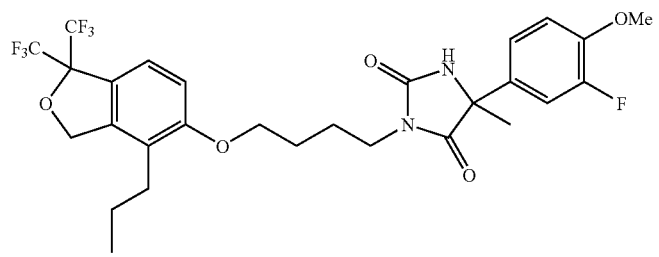 | 5-(3-fluoro-4-methoxyphenyl)-5-methyl-3-(4-(4-propyl-1,1-bis(trifluoromethyl)-1,3-dihydroisobenzofuran-5-yloxy)butyl)imidazolidine-2,4-dione |
| --- | --- | --- |

TABLE 1-5-continued

| Example 42 | 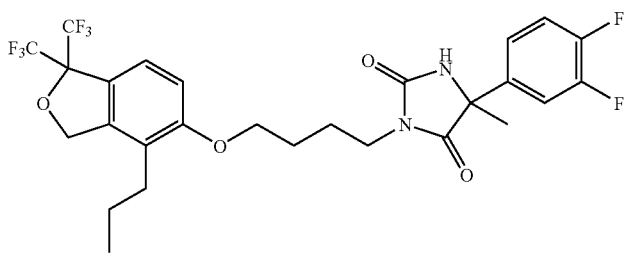 | 5-(3,4-difluorophenyl)-5-methyl-3-(4-(4-propyl-1,1-bis(trifluoromethyl)-1,3-dihydroisobenzofuran-5-yloxy)butyl)imidazolidine-2,4-dione |
| Example 43 | 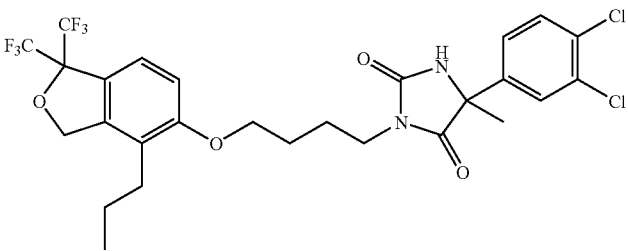 | 5-(3,4-dichlorophenyl)-5-methyl-3-(4-(4-propyl-1,1-bis(trifluoromethyl)-1,3-dihydroisobenzofuran-5-yloxy)butyl)imidazolidine-2,4-dione |
| Example 44 | 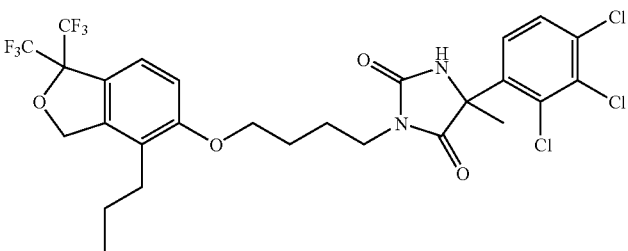 | 5-methyl-3-(4-(4-propyl-1,1-bis(trifluoromethyl)-1,3-dihydroisobenzofuran-5-yloxy)butyl)-5-(2,3,4-trichlorophenyl)imidazolidine-2,4-dione |
| Example 45 | 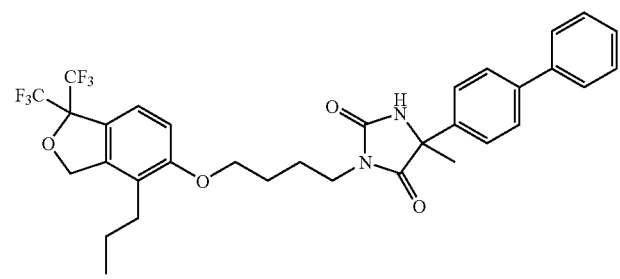 | 5-(biphenyl-4-yl)-5-methyl-3-(4-(4-propyl-1,1-bis(trifluoromethyl)-1,3-dihydroisobenzofuran-5-yloxy)butyl)imidazolidine-2,4-dione |
| Example 46 | 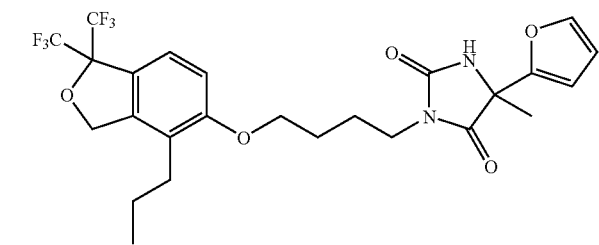 | 5-(furan-2-yl)-5-methyl-3-(4-(4-propyl-1,1-bis(trifluoromethyl)-1,3-dihydroisobenzofuran-5-yloxy)butyl)imidazolidine-2,4-dione |
| Example 47 | 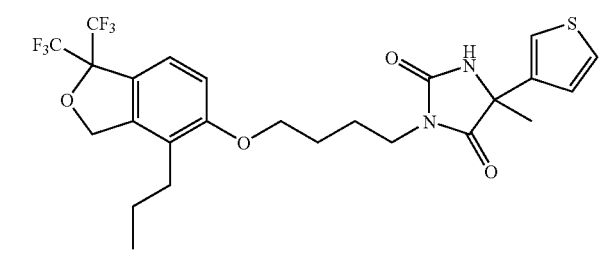 | 5-methyl-3-(4-(4-propyl-1,1-bis(trifluoromethyl)-1,3-dihydroisobenzofuran-5-yloxy)butyl)-5-(thiophen-3-yl)imidazolidine-2,4-dione |

TABLE 1-5-continued

| Exapmle 48 | 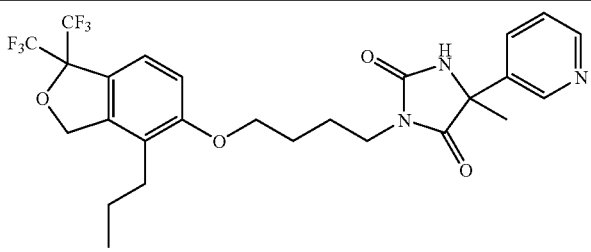 | 5-methyl-3-(4-(4-propyl-1,1-bis(trifluoromethyl)-1,3-dihydroisobenzofuran-5-yloxy)butyl)-5-(pyridin-3-yl)imidazolidine-2,4-dione |

TABLE 1-6

| Example 49 | 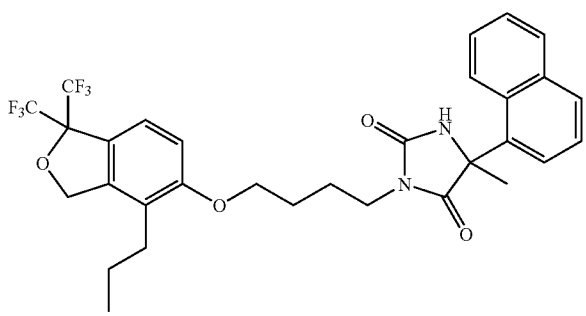 | 5-methyl-5-(naphthalen-1-yl)-3-(4-(4-propyl-1,1-bis(trifluoromethyl)-1,3-dihydroisobenzofuran-5-yloxy)butyl)imidazolidine-2,4-dione |
| Example 50 | 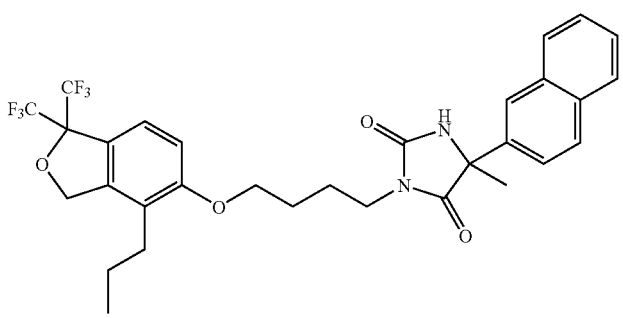 | 5-methyl-5-(naphthalen-2-yl)-3-(4-(4-propyl-1,1-bis(trifluoromethyl)-1,3-dihydroisobenzofuran-5-yloxy)butyl)imidazolidine-2,4-dione |
| Example 51 | 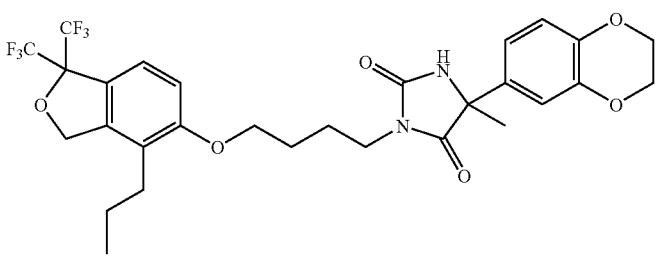 | 5-(2,3-dihydrobenzo[b][1,4]dioxin-6-yl)-5-methyl-3-(4-(4-propyl-1,1-bis(trifluoromethyl)-1,3-dihydroisobenzofuran-5-yloxy)butyl)imidazolidine-2,4-dione |
| Example 52 | 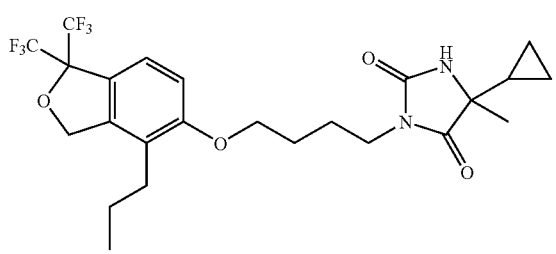 | 5-cyclopropyl-5-methyl-3-(4-(4-propyl-1,1-bis(trifluoromethyl)-1,3-dihydroisobenzofuran-5-yloxy)butyl)imidazolidine-2,4-dione |

TABLE 1-6-continued

| Example 53 | 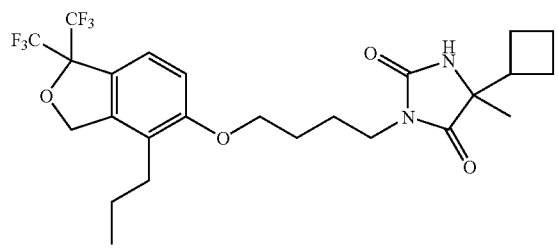 | 5-cyclobutyl-5-methyl-3-(4-(4-propyl-1,1-bis(trifluoromethyl)-1,3-dihydroisobenzofuran-5-yloxy)butyl)imidazolidine-2,4-dione |
| Example 54 | 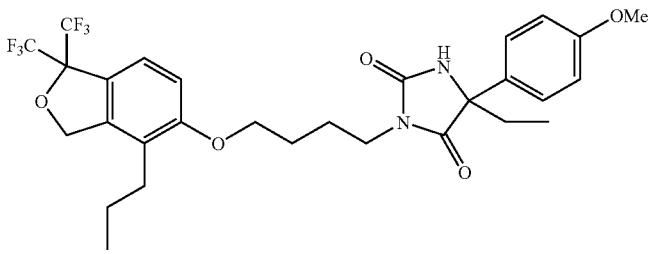 | 5-ethyl-5-(4-methoxyphenyl)-3-(4-(4-propyl-1,1-bis(trifluoromethyl)-1,3-dihydroisobenzofuran-5-yloxy)butyl)imidazolidine-2,4-dione |
| Example 55 | 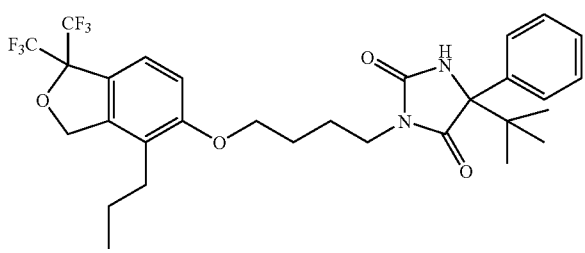 | 5-tert-butyl-5-phenyl-3-(4-(4-propyl-1,1-bis(trifluoromethyl)-1,3-dihydroisobenzofuran-5-yloxy)butyl)imidazolidine-2,4-dione |

TABLE 1-7

| Example 56 | 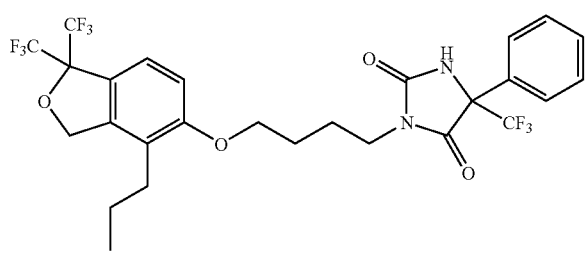 | 5-phenyl-3-(4-(4-propyl-1,1-bis(trifluoromethyl)-1,3-dihydroisobenzofuran-5-yloxy)butyl)-5-(trifluoromethyl)imidazolidine-2,4-dione |
| Example 57 | 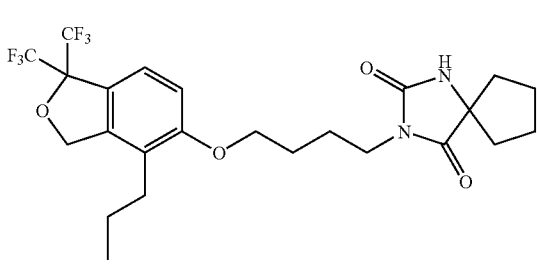 | 3-(4-(4-propyl-1,1-bis(trifluoromethyl)-1,3-dihydroisobenzofuran-5-yloxy)butyl)-1,3-diazaspiro[4.4]nonane-2,4-dione |

TABLE 1-7-continued

| Example 58 | 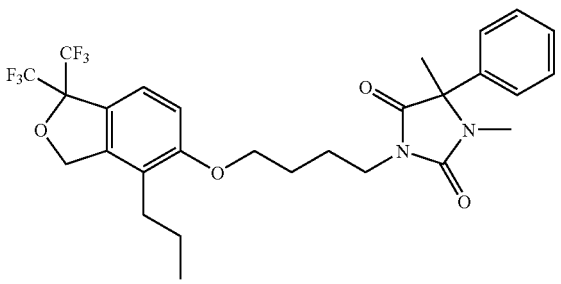 | 1,5-dimethyl-5-phenyl-3-(4-(4-propyl-1,1-bis(trifluoromethyl)-1,3-dihydroisobenzofuran-5-yloxy)butyl)imidazolidine-2,4-dione |
| --- | --- | --- |
| Example 59 | 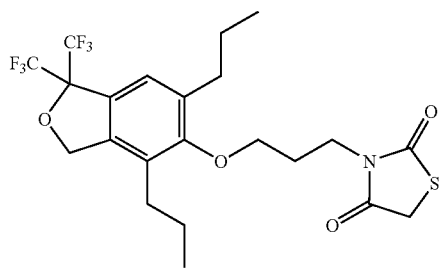 | 3-(3-(4,6-dipropyl-1,1-bis(trifluoromethyl)-1,3-dihydroisobenzofuran-5-yloxy)propyl)thiazolidine-2,4-dione |
| Example 60 | 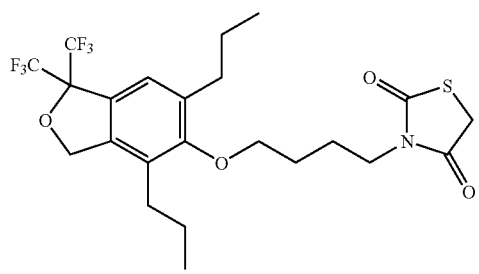 | 3-(4-(4,6-dipropyl-1,1-bis(trifluoromethyl)-1,3-dihydroisobenzofuran-5-yloxy)butyl)thiazolidine-2,4-dione |
| Example 61 | 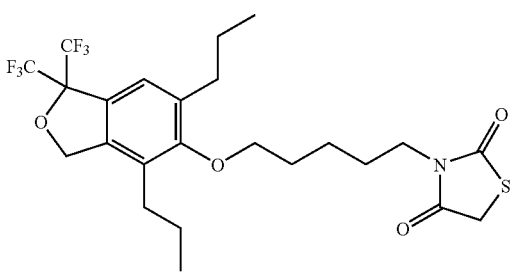 | 3-(5-(4,6-dipropyl-1,1-bis(trifluoromethyl)-1,3-dihydroisobenzofuran-5-yloxy)pentyl)thiazolidine-2,4-dione |
| Example 62 | 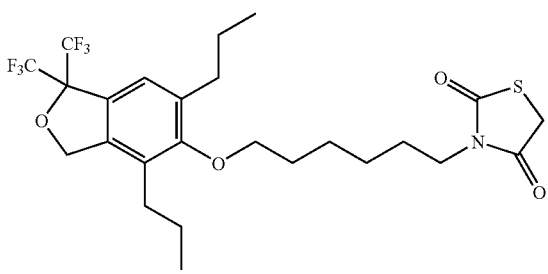 | 3-(6-(4,6-dipropyl-1,1-bis(trifluoromethyl)-1,3-dihydroisobenzofuran-5-yloxy)hexyl)thiazolidine-2,4-dione |
| Example 63 | 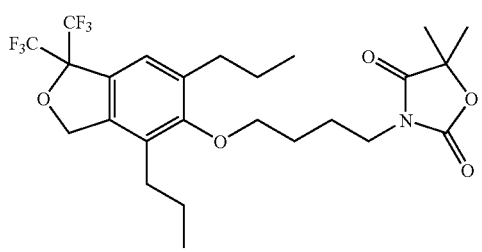 | 3-(4-(4,6-dipropyl-1,1-bis(trifluoromethyl)-1,3-dihydroisobenzofuran-5-yloxy)butyl)-5,5-dimethyloxazolidine-2,4-dione |

TABLE 1-7-continued

| Example 64 | 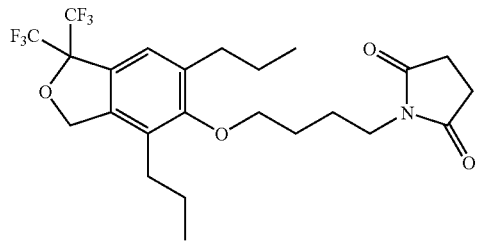 | 1-(4-(4,6-dipropyl-1,1-bis(trifluoromethyl)-1,3-dihydroisobenzofuran-5-yloxy)butyl)pyrrolidine-2,5-dione |

TABLE 1-8

| Example 65 | 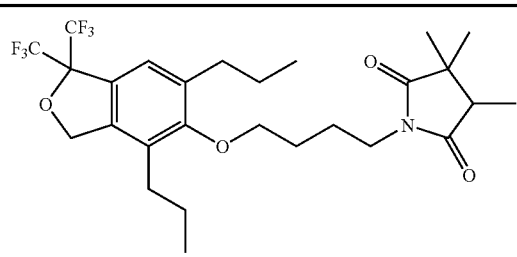 | 1-(4-(4,6-dipropyl-1,1-bis(trifluoromethyl)-1,3-dihydroisobenzofuran-5-yloxy)butyl)-3,3,4-trimethylpyrrolidine-2,5-dione |
| Example 66 | 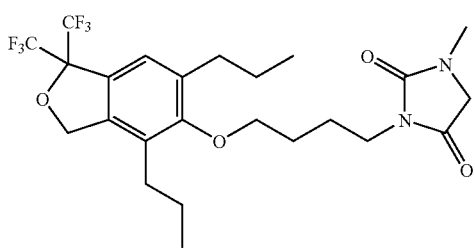 | 3-(4-(4,6-dipropyl-1,1-bis(trifluoromethyl)-1,3-dihydroisobenzofuran-5-yloxy)butyl)-1-methylimidazolidine-2,4-dione |
| Example 67 | 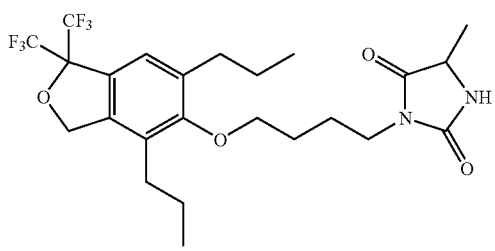 | 3-(4-(4,6-dipropyl-1,1-bis(trifluoromethyl)-1,3-dihydroisobenzofuran-5-yloxy)butyl)-5-methylimidazolidine-2,4-dione |
| Example 68 | 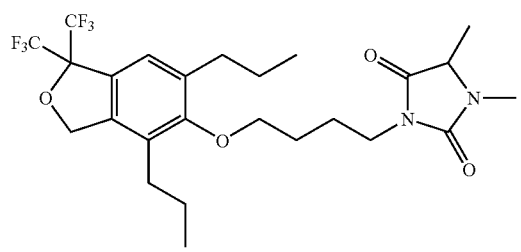 | 3-(4-(4,6-dipropyl-1,1-bis(trifluoromethyl)-1,3-dihydroisobenzofuran-5-yloxy)butyl)-1,5-dimethylimidazolidine-2,4-dione |
| Example 69 | 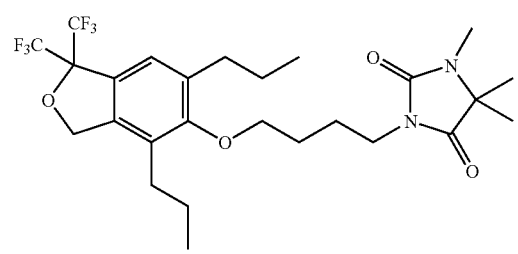 | 3-(4-(4,6-dipropyl-1,1-bis(trifluoromethyl)-1,3-dihydroisobenzofuran-5-yloxy)butyl)-1,5,5-trimethylimidazolidine-2,4-dione |

TABLE 1-8-continued

| Example 70 | 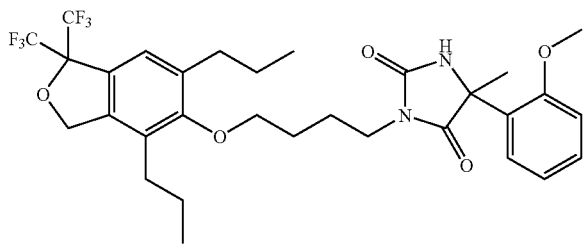 | 3-(4-(4,6-dipropyl-1,1-bis(trifluoromethyl)-1,3-dihydroisobenzofuran-5-yloxy)butyl)-5-(2-methoxyphenyl)-5-methylimidazolidine-2,4-dione |
| Example 71 | 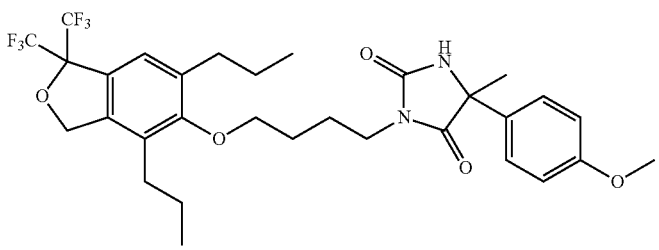 | 3-(4-(4,6-dipropyl-1,1-bis(trifluoromethyl)-1,3-dihydroisobenzofuran-5-yloxy)butyl)-5-(4-methoxyphenyl)-5-methylimidazolidine-2,4-dione |
| Example 72 | 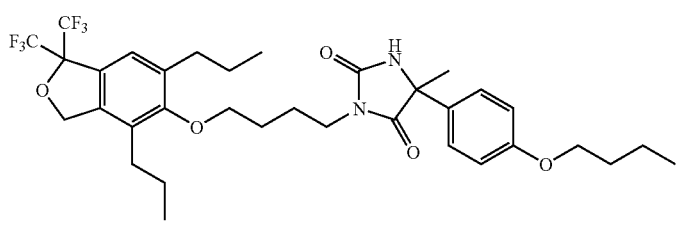 | 5-(4-butoxyphenyl)-3-(4-(4,6-dipropyl-1,1-bis(trifluoromethyl)-1,3-dihydroisobenzofuran-5-yloxy)butyl)-5-methylimidazolidine-2,4-dione |

TABLE 1-9

| Example 73 | 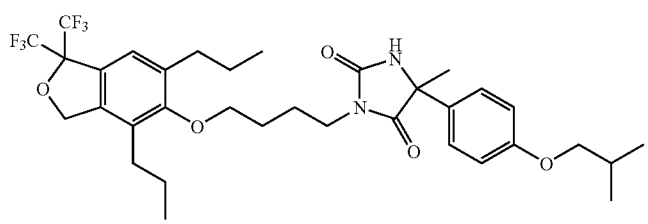 | 3-(4-(4,6-dipropyl-1,1-bis(trifluoromethyl)-1,3-dihydroisobenzofuran-5-yloxy)butyl)-5-(4-isobutoxyphenyl)-5-methylimidazolidine-2,4-dione |
| Example 74 | 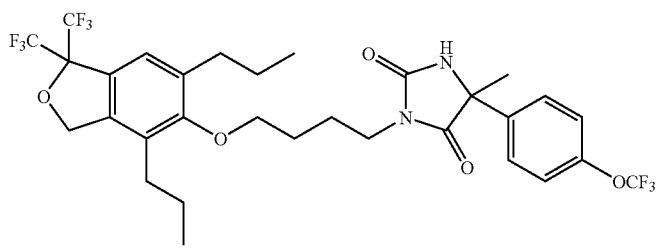 | 3-(4-(4,6-dipropyl-1,1-bis(trifluoromethyl)-1,3-dihydroisobenzofuran-5-yloxy)butyl)-5-methyl-5-(4-(trifluoromethoxy)phenyl)imidazolidine-2,4-dione |
| Example 75 | 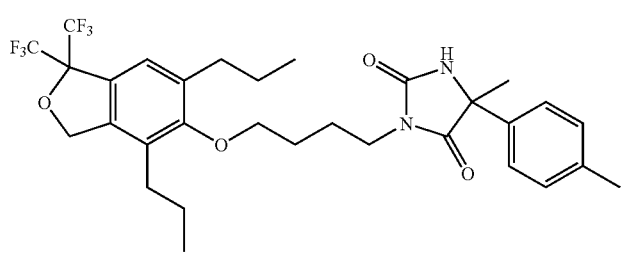 | 3-(4-(4,6-dipropyl-1,1-bis(trifluoromethyl)-1,3-dihydroisobenzofuran-5-yloxy)butyl)-5-methyl-5-p-tolylimidazolidine-2,4-dione |

TABLE 1-9-continued

| Example 76 | 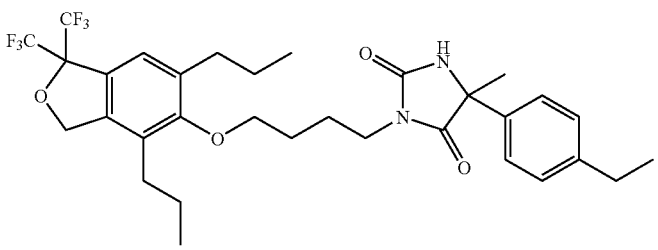 | 3-(4-(4,6-dipropyl-1,1-bis(trifluoromethyl)-1,3-dihydroisobenzofuran-5-yloxy)butyl)-5-(4-ethylphenyl-5-methylimidazolidine-2,4-dione |
| --- | --- | --- |
| Example 77 | 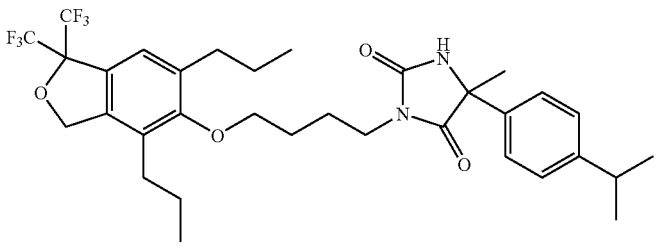 | 3-(4-(4,6-dipropyl-1,1-bis(trifluoromethyl)-1,3-dihydroisobenzofuran-5-yloxy)butyl)-5-(4-isopropylphenyl)-5-methylimidazolidine-2,4-dione |
| Example 78 | 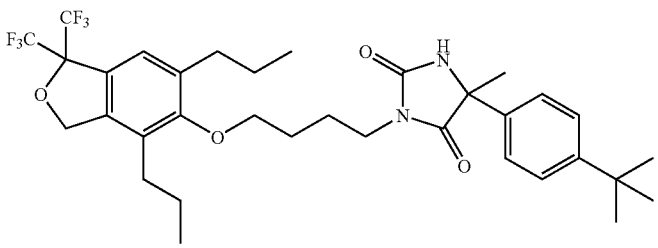 | 5-(4-tert-butylphenyl)-3-(4-(4,6-dipropyl-1,1-bis(trifluoromethyl)-1,3-dihydroisobenzofuran-5-yloxy)butyl)-5-methylimidazolidine-2,4-dione |
| Example 79 | 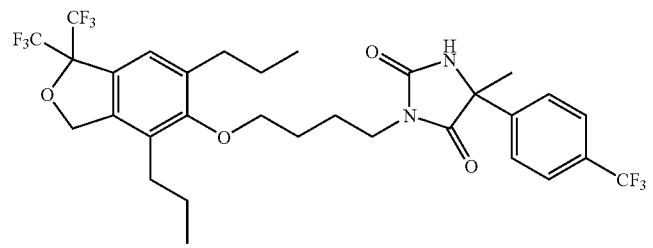 | 3-(4-(4,6-dipropyl-1,1-bis(trifluoromethyl)-1,3-dihydroisobenzofuran-5-yloxy)butyl)-5-methyl-5-(4-(trifluoromethyl)phenyl)imidazolidine-2,4-dione |
| Example 80 | 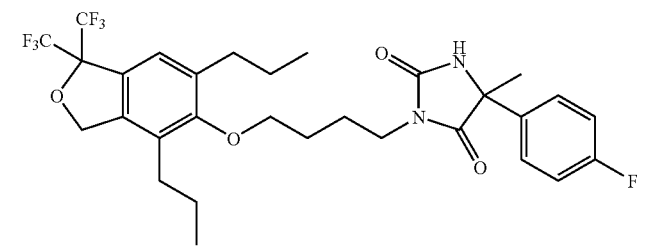 | 3-(4-(4,6-dipropyl-1,1-bis(trifluoromethyl)-1,3-dihydroisobenzofuran-5-yloxy)butyl)-5-(4-fluorophenyl)-5-methylimidazolidine-2,4-dione |

TABLE 1-10

| Example 81 | 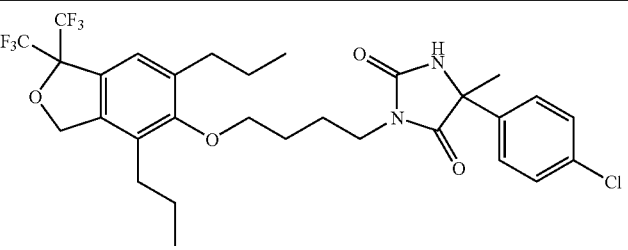 | 5-(4-chlorophenyl)-3-(4-(4,6-dipropyl-1,1-bis(trifluoromethyl)-1,3-dihydroisobenzofuran-5-yloxy)butyl)-5-methylimidazolidine-2,4-dione |
| --- | --- | --- |

TABLE 1-10-continued

| Example | Structure | Name |
|---|---|---|
| Example 82 | 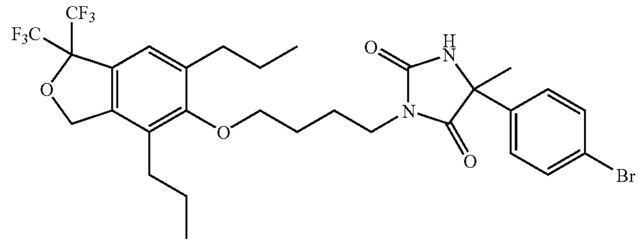 | 5-(4-bromophenyl)-3-(4-(4,6-dipropyl-1,1-bis(trifluoromethyl)-1,3-dihydroisobenzofuran-5-yloxy)butyl)-5-methylimidazolidine-2,4-dione |
| Example 83 | 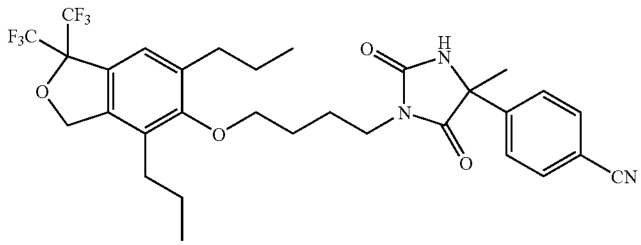 | 4-(1-(4-(4,6-dipropyl-1,1-bis(trifluoromethyl)-1,3-dihydroisobenzofuran-5-yloxy)butyl)-4-methyl-2,5-dioxoimidazolidin-4-yl)benzonitrile |
| Example 84 | 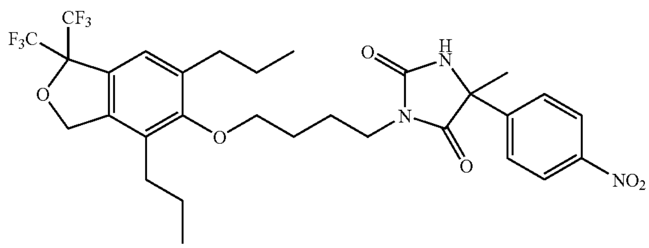 | 3-(4-(4,6-dipropyl-1,1-bis(trifluoromethyl)-1,3-dihydroisobenzofuran-5-yloxy)butyl)-5-methyl-5-(4-nitrophenyl)imidazolidine-2,4-dione |
| Example 85 | 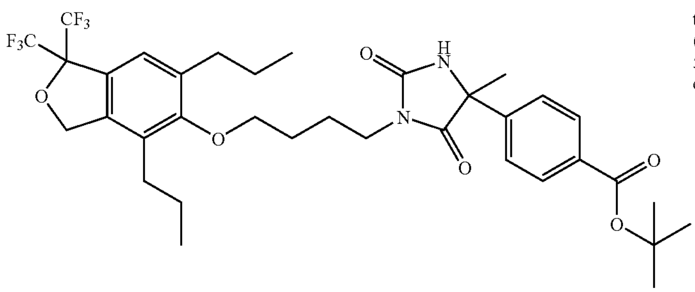 | tert-butyl 4-(1-(4-(4,6-dipropyl-1,1-bis(trifluoromethyl)-1,3-dihydroisobenzofuran-5-yloxy)butyl)-4-methyl-2,5-dioxoimidazolidin-4-yl)benzoate |
| Example 86 | 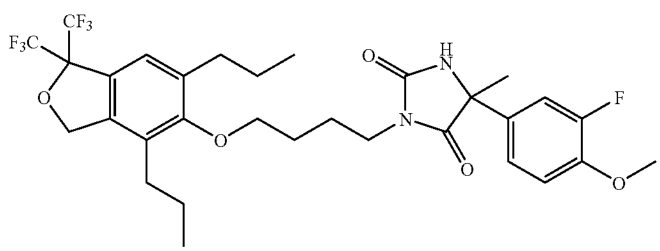 | 3-(4-(4,6-dipropyl-1,1-bis(trifluoromethyl)-1,3-dihydroisobenzofuran-5-yloxy)butyl)-5-(3-fluoro-4-methoxyphenyl)-5-methylimidazolidine-2,4-dione |
| Example 87 | 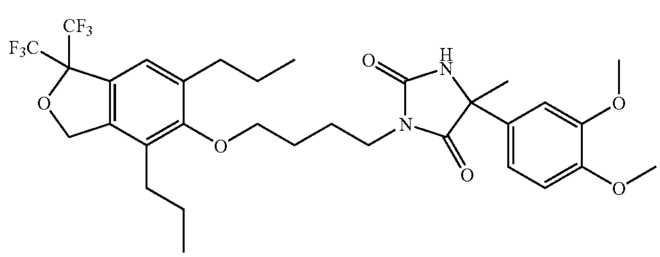 | 5-(3,4-dimethoxyphenyl)-3-(4-(4,6-dipropyl-1,1-bis(trifluoromethyl)-1,3-dihydroisobenzofuran-5-yloxy)butyl)-5-methylimidazolidine-2,4-dione |

TABLE 1-10-continued

| Example 88 | 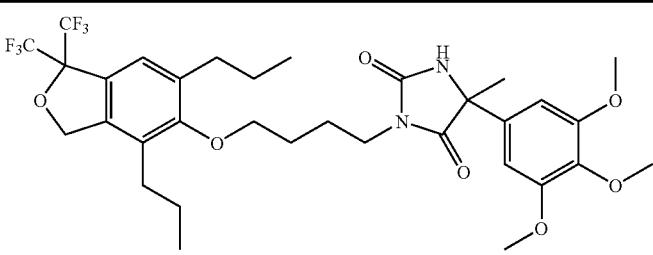 | 3-(4-(4,6-dipropyl-1,1-bis(trifluoromethyl)-1,3-dihydroisobenzofuran-5-yloxy)butyl)-5-methyl-5-(3,4,5-trimethoxyphenyl)imidazolidine-2,4-dione |

TABLE 1-11

| Example 89 | 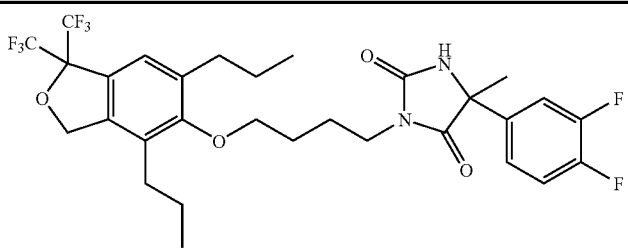 | 5-(3,4-difluorophenyl)-3-(4-(4,6-dipropyl-1,1-bis(trifluoromethyl)-1,3-dihydroisobenzofuran-5-yloxy)butyl)-5-methylimidazolidine-2,4-dione |
| Example 90 | 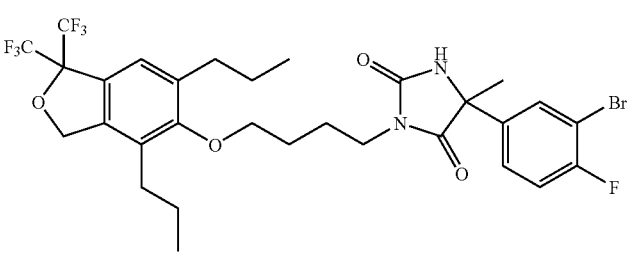 | 5-(3-bromo-4-fluorophenyl)-3-(4-(4,6-dipropyl-1,1-bis(trifluoromethyl)-1,3-dihydroisobenzofuran-5-yloxy)butyl)-5-methylimidazolidine-2,4-dione |
| Example 91 | 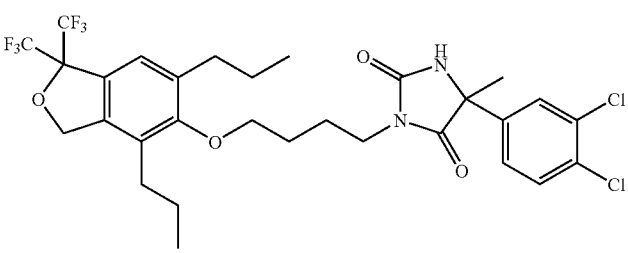 | 5-(3,4-dichlorophenyl)-3-(4-(4,6-dipropyl-1,1-bis(trifluoromethyl)-1,3-dihydroisobenzofuran-5-yloxy)butyl)-5-methylimidazolidine-2,4-dione |
| Example 92 | 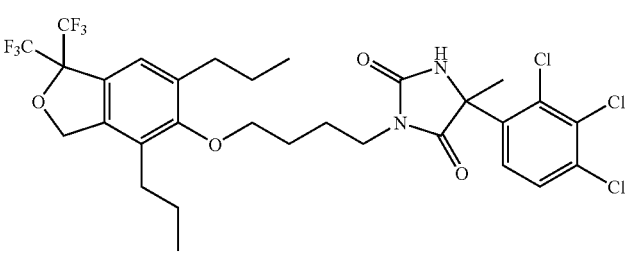 | 3-(4-(4,6-dipropyl-1,1-bis(trifluoromethyl)-1,3-dihydroisobenzofuran-5-yloxy)butyl)-5-methyl-5-(2,3,4-trichlorophenyl)imidazolidine-2,4-dione |
| Example 93 | 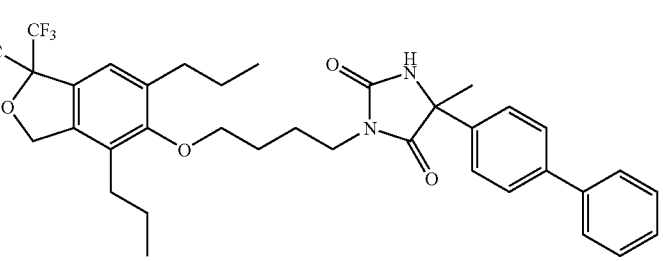 | 5-(biphenyl-4-yl)-3-(4-(4,6-dipropyl-1,1-bis(trifluoromethyl)-1,3-dihydroisobenzofuran-5-yloxy)butyl)-5-methylimidazolidine-2,4-dione |

TABLE 1-11-continued

Example 94 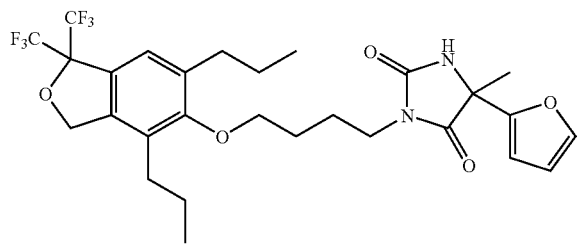
3-(4-(4,6-dipropyl-1,1-bis(trifluoromethyl)-1,3-dihydroisobenzofuran-5-yloxy)butyl)-5-(furan-2-yl)-5-methylimidazolidine-2,4-dione Example 95 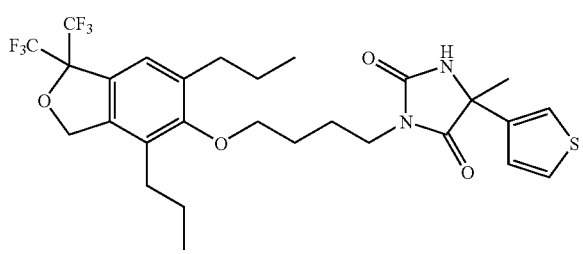
3-(4-(4,6-dipropyl-1,1-bis(trifluoromethyl)-1,3-dihydroisobenzofuran-5-yloxy)butyl)-5-methyl-5-(thiophen-3-yl)imidazolidine-2,4-dione Example 96 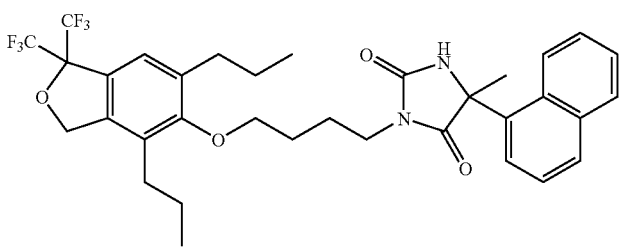
3-(4-(4,6-dipropyl-1,1-bis(trifluoromethyl)-1,3-dihydroisobenzofuran-5-yloxy)butyl)-5-methyl-5-(naphthalen-1-yl)imidazolidine-2,4-dione

TABLE 1-12

Example 97 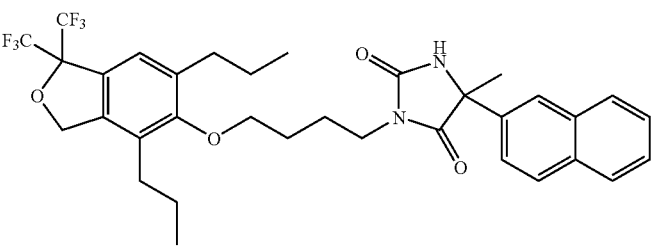
3-(4-(4,6-dipropyl-1,1-bis(trifluoromethyl)-1,3-dihydroisobenzofuran-5-yloxy)butyl)-5-methyl-5-(naphthalen-2-yl)imidazolidine-2,4-dione Example 98 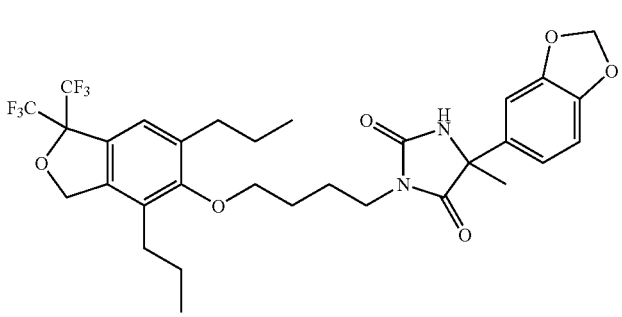
5-(benzo[d][1,3]dioxol-5-yl)-3-(4-(4,6-dipropyl-1,1-bis(trifluoromethyl)-1,3-dihydroisobenzofuran-5-yloxy)butyl)-5-methylimidazolidine-2,4-dione TABLE 1-12-continued

| Example 99 | 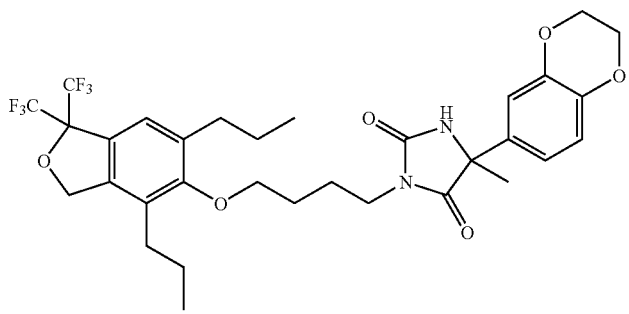 | 5-(2,3-dihydrobenzo[b][1,4]dioxin-6-yl)-3-(4-(4,6-dipropyl-1,1-bis(trifluoromethyl)-1,3-dihydroisobenzofuran-5-yloxy)butyl)-5-methylimidazolidine-2,4-dione |
| --- | --- | --- |
| Example 100 | 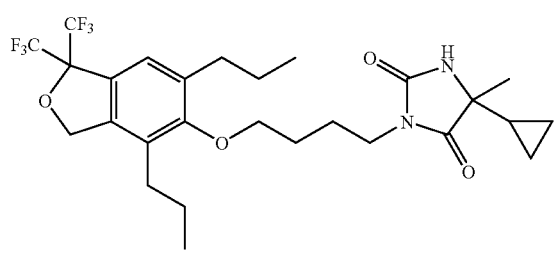 | 5-cyclopropyl-3-(4-(4,6-dipropyl-1,1-bis(trifluoromethyl)-1,3-dihydroisobenzofuran-5-yloxy)butyl)-5-methylimidazolidine-2,4-dione |
| Example 101 | 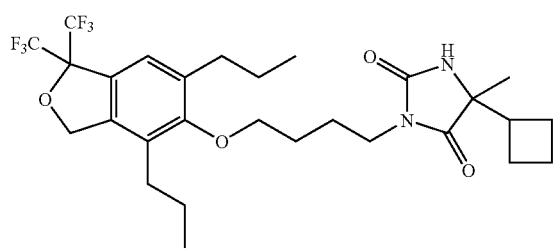 | 5-cyclobutyl-3-(4-(4,6-dipropyl-1,1-bis(trifluoromethyl)-1,3-dihydroisobenzofuran-5-yloxy)butyl)-5-methylimidazolidine-2,4-dione |
| Example 102 | 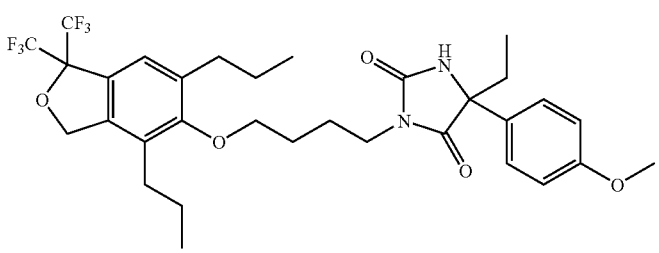 | 3-(4-(4,6-dipropyl-1,1-bis(trifluoromethyl)-1,3-dihydroisobenzofuran-5-yloxy)butyl)-5-ethyl-5-(4-methoxyphenyl)imidazolidine-2,4-dione |
| Example 103 | 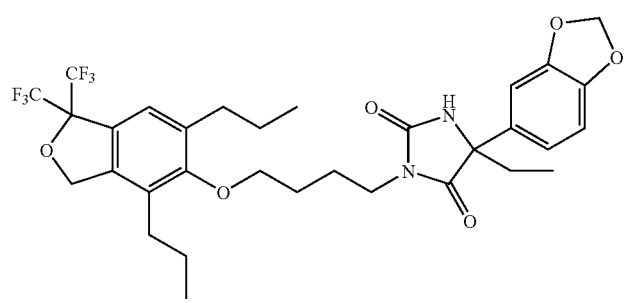 | 5-(benzo[d][1,3]dioxol-5-yl)-3-(4-(4,6-dipropyl-1,1-bis(trifluoromethyl)-1,3-dihydroisobenzofuran-5-yloxy)butyl)-5-ethylimidazolidine-2,4-dione |

TABLE 1-13

| Example 104 | 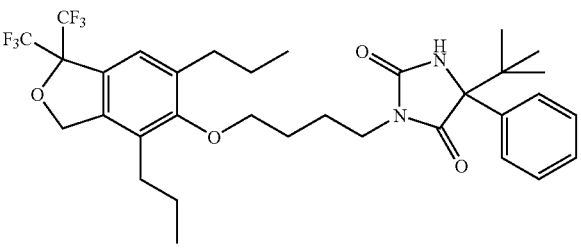 | 5-tert-butyl-3-(4-(4,6-dipropyl-1,1-bis(trifluoromethyl)-1,3-dihydroisobenzofuran-5-yloxy)butyl-5-phenylimidazolidine-2,4-dione |
| --- | --- | --- |
| Example 105 | 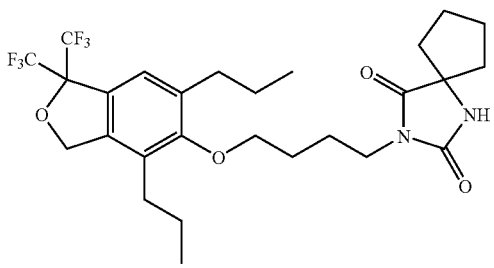 | 3-(4-(4,6-dipropyl-1,1-bis(trifluoromethyl)-1,3-dihydroisobenzofuran-5-yloxy)butyl)-1,3-diazaspiro[4.4]nonane-2,4-dione |
| Example 106 | 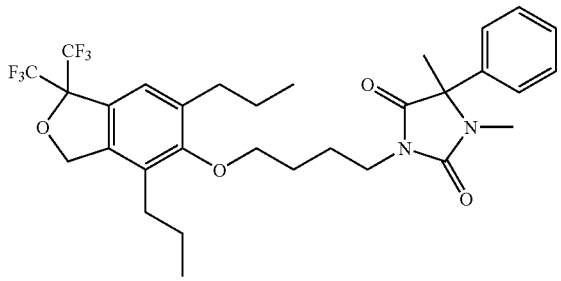 | 3-(4-(4,6-dipropyl-1,1-bis(trifluoromethyl)-1,3-dihydroisobenzofuran-5-yloxy)butyl)-1,5-dimethyl-5-phenylimidazolidine-2,4-dione |
| Example 107 | 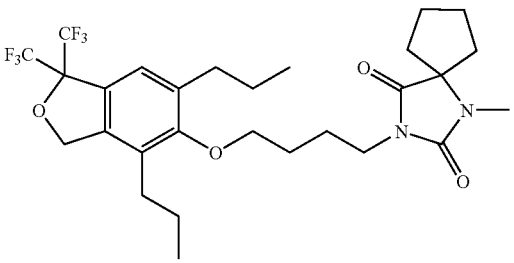 | 3-(4-(4,6-dipropyl-1,1-bis(trifluoromethyl)-1,3-dihydroisobenzofuran-5-yloxy)butyl)-1-methyl-1,3-diazaspiro[4.4]nonane-2,4-dione |
| Example 108 | 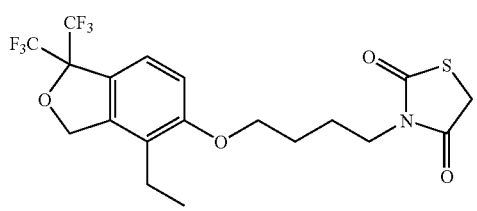 | 3-(4-(4-ethyl-1,1-bis(trifluoromethyl)-1,3-dihydroisobenzofuran-5-yloxy)butyl)thiazolidine-2,4-dione |
| Example 109 | 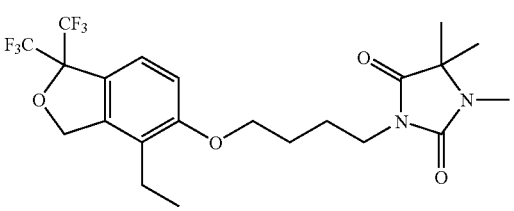 | 3-(4-(4-ethyl-1,1-bis(trifluoromethyl)-1,3-dihydroisobenzofuran-5-yloxy)butyl)-1,5,5-trimethylimidazolidine-2,4-dione |

TABLE 1-13-continued

| Example 110 | 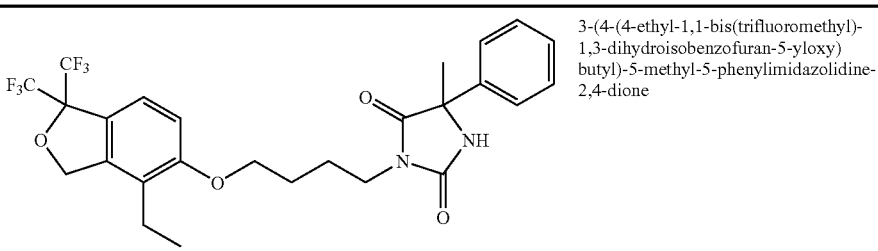 | 3-(4-(4-ethyl-1,1-bis(trifluoromethyl)-1,3-dihydroisobenzofuran-5-yloxy)butyl)-5-methyl-5-phenylimidazolidine-2,4-dione |
| Example 111 | 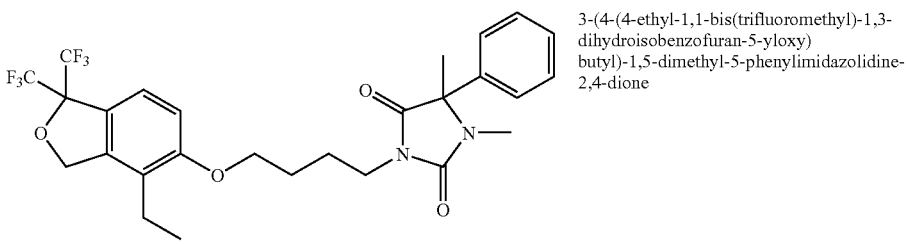 | 3-(4-(4-ethyl-1,1-bis(trifluoromethyl)-1,3-dihydroisobenzofuran-5-yloxy)butyl)-1,5-dimethyl-5-phenylimidazolidine-2,4-dione |

TABLE 1-14

| Example 112 | 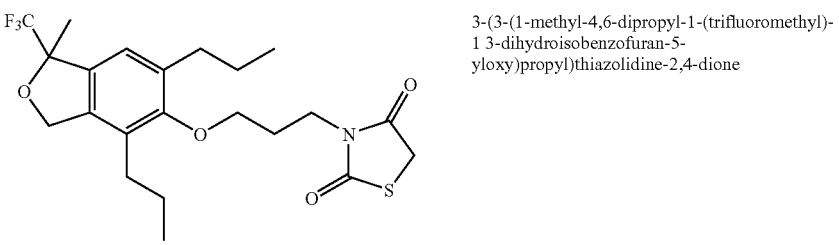 | 3-(3-(1-methyl-4,6-dipropyl-1-(trifluoromethyl)-1 3-dihydroisobenzofuran-5-yloxy)propyl)thiazolidine-2,4-dione |
| Example 113 | 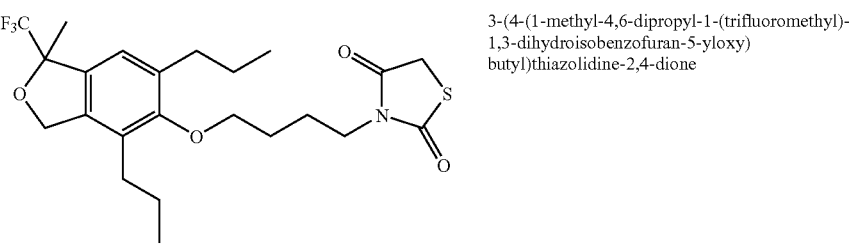 | 3-(4-(1-methyl-4,6-dipropyl-1-(trifluoromethyl)-1,3-dihydroisobenzofuran-5-yloxy)butyl)thiazolidine-2,4-dione |
| Example 114 | 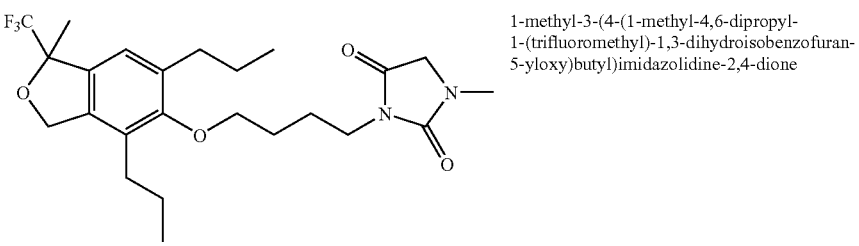 | 1-methyl-3-(4-(1-methyl-4,6-dipropyl-1-(trifluoromethyl)-1,3-dihydroisobenzofuran-5-yloxy)butyl)imidazolidine-2,4-dione |
| Example 115 | 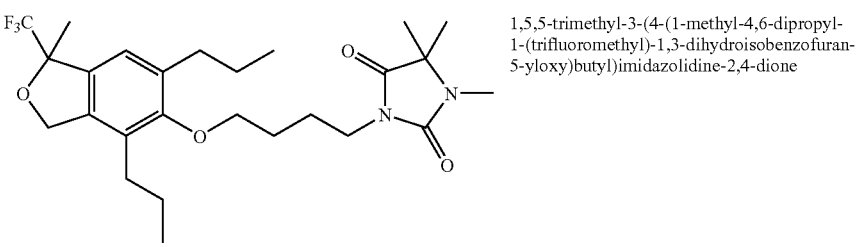 | 1,5,5-trimethyl-3-(4-(1-methyl-4,6-dipropyl-1-(trifluoromethyl)-1,3-dihydroisobenzofuran-5-yloxy)butyl)imidazolidine-2,4-dione |

TABLE 1-15

| | |
|---|---|
| Example 62 | ¹H-NMR (CDCl₃) δ: 0.95 (3H, t, J = 7.3 Hz), 0.97 (3H, t, J = 7.3 Hz), 1.36-1.48 (2H, m), 1.49-1.72 (8H, m), 1.76-1.86 (2H, m), 2.47 (2H, t, J = 7.8 Hz), 2.60 (2H, t, J = 7.8 Hz), 3.65 (2H, t, J = 7.5 Hz), 3.76 (2H, t, J = 6.5 Hz), 3.95 (2H, s), 5.27 (2H, s), 7.15 (1H, s) |
| Example 63 | ¹H-NMR (CDCl₃) δ: 0.92-0.98 (6H, m), 1.51-1.68 (10H, m), 1.79-1.97 (4H, m), 2.46 (2H, t, J = 7.8 Hz), 2.60 (2H, t, J = 7.8 Hz), 3.65 (2H, t, J = 7.1 Hz), 3.80 (2H, t, J = 6.1 Hz), 5.27 (2H, s), 7.16 (1H, s). |
| Example 64 | ¹H-NMR (CDCl₃) δ: 0.94 (3H, t, J = 7.3 Hz), 0.96 (3H, t, J = 7.3 Hz), 1.48-1.70 (4H, m), 1.76-1.88 (4H, m), 2.47 (2H, t, J = 7.8 Hz), 2.60 (2H, t, J = 7.8 Hz), 2.73 (4H, s), 3.63 (2H, t, J = 6.8 Hz), 3.79 (2H, t, J = 5.8 Hz), 5.27 (2H, s), 7.15 (1H, s). |
| Example 65 | ¹H-NMR (CDCl₃) δ: 0.92-0.97 (6H, m), 1.15 (3H, s), 1.22 (3H, d, J = 7.3 Hz), 1.31 (3H, s), 1.47-1.67 (5H, m), 1.80-1.83 (3H, m), 2.44-2.48 (2H, m), 2.54-2.61 (3H, m), 3.58 (2H, t, J = 6.7 Hz), 3.78 (2H, t, J = 5.9 Hz), 5.26 (2H, s), 7.15 (1H, s). |
| Example 70 | ¹H-NMR (CDCl₃) δ: 0.90-0.96 (6H, m), 1.47-1.70 (4H, m), 1.77 (3H, s), 1.80-1.94 (4H, m), 2.43-2.50 (2H, m), 2.56-2.63 (2H, m), 3.68 (2H, t, J = 6.6 Hz), 3.80 (2H, t, J = 5.6 Hz), 3.88 (3H, s), 5.26 (2H, s), 6.27 (1H, brs), 6.92-6.96 (2H, m), 7.15 (1H, s), 7.30 (1H, ddd, J = 1.6, 8.2, 8.2 Hz), 7.51 (1H, dd, J = 1.6, 8.2 Hz). |
| Example 72 | ¹H-NMR (CDCl₃) δ: 0.88-1.00 (9H, m), 1.43-1.66 (8H, m), 1.69-1.90 (7H, m), 2.44 (2H, t, J = 7.6 Hz), 2.57 (2H, t, J = 7.6 Hz), 3.62 (2H, t, J = 6.6 Hz), 3.76 (2H, t, J = 5.6 Hz), 3.94 (2H, t, J = 6.6 Hz), 5.25 (2H, s), 5.76 (1H, brs), 6.89 (2H, d, J = 8.6 Hz), 7.14 (1H, s), 7.37 (2H, d, J = 8.6 Hz). |
| Example 73 | ¹H-NMR (CDCl₃) δ: 0.88-0.97 (6H, m), 1.01 (6H, d, J = 6.6 Hz), 1.48-1.66 (4H, m), 1.70-1.92 (7H, m), 2.01-2.12 (1H, m), 2.44 (2H, t, J = 7.6 Hz), 2.57 (2H, t, J = 7.6 Hz), 3.62 (2H, t, J = 6.6 Hz), 3.69 (2H, d, J = 6.3 Hz), 3.76 (2H, t, J = 5.6 Hz), 5.25 (2H, s), 5.80 (1H, brs), 6.89 (2H, d, J = 8.6 Hz), 7.14 (1H, s), 7.37 (2H, d, J = 8.6 Hz). |
| Example 75 | ¹H-NMR (CDCl₃) δ: 0.87-0.96 (6H, m), 1.48-1.65 (4H, m), 1.75-1.90 (4H, m), 2.33 (3H, s), 2.40-2.47 (2H, m), 2.53-2.60 (2H, m), 3.61 (2H, t, J = 6.3 Hz), 3.76 (2H, t, J = 5.6 Hz), 5.25 (2H, s), 6.13 (1H, brs), 7.14 (1H, s), 7.19 (2H, d, J = 8.2 Hz), 7.37 (2H, d, J = 8.2 Hz). |
| Example 76 | ¹H-NMR (CDCl₃) δ: 0.87-0.96 (6H, m), 1.21 (3H, t, J = 7.6 Hz), 1.48-1.66 (4H, m), 1.73-1.93 (7H, m), 2.41-2.47 (2H, m), 2.54-2.60 (2H, m), 2.66 (2H, q, J = 7.6 Hz), 3.62 (2H, t, J = 6.6 Hz), 3.76 (2H, t, J = 5.6 Hz), 5.25 (2H, s), 5.87 (1H, brs), 7.14 (1H, s), 7.21 (2H, d, J = 8.2 Hz), 7.39 (2H, d, J = 8.2 Hz). |
| Example 78 | ¹H-NMR (CDCl₃) δ: 0.88-0.97 (6H, m), 1.30 (9H, s), 1.51-1.63 (4H, m), 1.76-1.92 (7H, m), 2.41-2.48 (2H, m), 2.54-2.61 (2H, m), 3.62 (2H, t, J = 6.6 Hz), 3.77 (2H, t, J = 5.9 Hz), 5.25 (2H, s), 5.62 (1H, brs), 7.14 (1H, s), 7.39-7.41 (4H, m). |
| Example 79 | ¹H-NMR (CDCl₃) δ: 0.86-0.96 (6H, m), 1.45-1.65 (4H, m), 1.74-1.91 (7H, m), 2.40-2.47 (2H, m), 2.53-2.60 (2H, m), 3.63 (2H, t, J = 6.9 Hz), 3.76 (2H, t, J = 5.3 Hz), 5.25 (2H, s), 6.09 (1H, brs), 7.14 (1H, s), 7.65-7.67 (4H, m). |
| Example 83 | ¹H-NMR (CDCl₃) δ: 0.87-0.96 (6H, m), 1.47-1.65 (4H, m), 1.76-1.91 (7H, m), 2.40-2.46 (2H, m), 2.53-2.59 (2H, m), 3.63 (2H, t, J = 6.6 Hz), 3.76 (2H, t, J = 5.6 Hz), 5.25 (2H, s), 6.08 (1H, brs), 7.14 (1H, s), 7.65-7.67 (4H, m). |
| Example 84 | ¹H-NMR (CDCl₃) δ: 0.87-0.96 (6H, m), 1.47-1.68 4H, m), 1.74-1.91 (7H, m), 2.40-2.47 (2H, m), 2.53-2.60 (2H, m), 3.62 (2H, t, J = 6.6 Hz), 3.76 (2H, t, J = 5.6 Hz), 5.25 (2H, s), 6.11 (1H, brs), 7.14 (1H, s), 7.39 (2H, d, J = 8.6 Hz), 7.51 (2H, d, J = 8.6 Hz). |
| Example 105 | ¹H-NMR (CDCl₃) δ: 0.92-0.98 (6H, m), 1.51-1.68 (4H, m), 1.78-1.95 (10H, m), 2.15-2.20 (2H, m), 2.46 (2H, t, J = 7.8 Hz), 2.60 (2H, t, J = 7.7 Hz), 3.62 (2H, t, J = 6.8 Hz), 3.80 (2H, t, J = 5.9 Hz), 5.26 (2H, s), 5.87 (1H, brs), 7.15 (1H, s). |
| Example 110 | ¹H-NMR (CDCl₃) δ: 1.08 (3H, t, J = 7.6 Hz), 1.80-1.85 (7H, m), 2.49 (2H, q, J = 7.6 Hz), 3.55-3.64 (2H, m), 3.99 (2H, t, J = 5.7 Hz), 5.28 (2H, s), 6.46 (1H, brs), 6.81 (1H, d, J = 8.3 Hz), 7.26 (1H, m), 7.31-7.41 (3H, m), 7.48-7.58 (2H, m). |
| Example 112 | ¹H-NMR (CDCl₃) δ: 0.94-1.00 (6H, m), 1.50-1.66 (7H, m), 2.09-2.16 (2H, m), 2.39-2.48 (2H, m), 2.49-2.63 (2H, m), 3.82 (2H, t, J = 6.1 Hz), 3.91 (2H, t, J = 7.2 Hz), 3.96 (2H, s), 5.10 (2H, q, J = 10.8 Hz), 6.94 (1H, s). |

Test Example 1

Transactivation Assay

<Construction of Plasmid>

The ligand-binding domain (LBD) of a human LXRα and LXRβ cDNA was inserted adjacent to an yeast GAL4-transcription factor DNA-binding domain (DBD) of a mammal expression vector pBIND (Promega) to prepare an expression construct, thereby to produce pBIND-LXRα/GAL4 and pBIND-LXRβ/GAL4, respectively. PG5luc, a GAL4-responsive reporter construct, is a known vector that is available from Promega, and contains 5 copies of GAL4-response element located adjacent to the promoter as well as a luciferase reporter gene.

<Assay>

Figure 1:
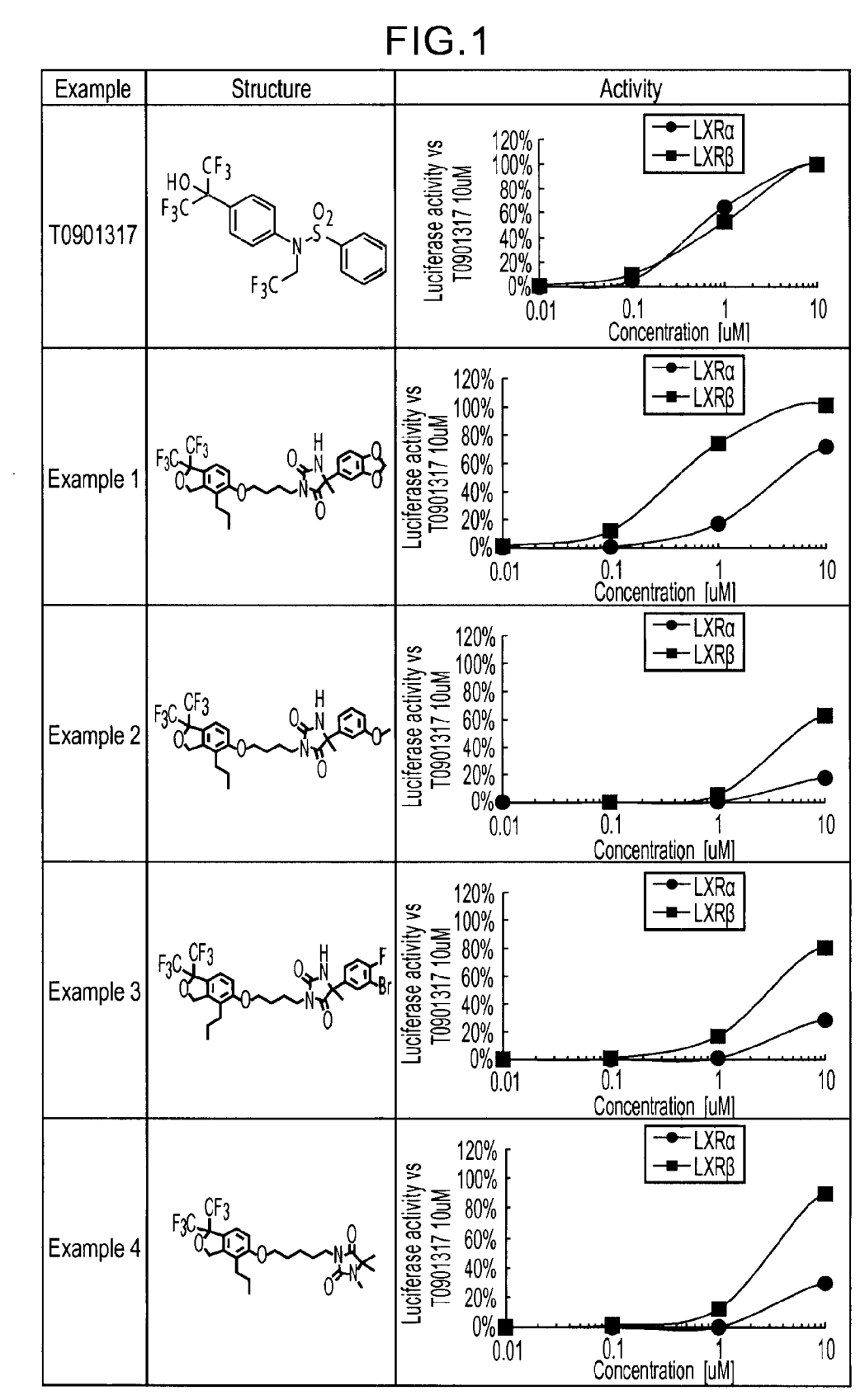

An LXRα/GAL4 or LXRβ/GAL4 hybrid and GAL4-responsive reporter vector pG5luc-stable-expression CHOK-1 cells were seeded under 5% $CO_2$ wet atmosphere at 37° C., at 20,000 cells/well on a 96-well plate containing HAM-F12 medium containing 10% immobilized bovine fetal serum, 100 units/ml of penicillin G, and 100 μg/ml of streptomycin sulfate. 24 hours later, the medium with a test compound dissolved therein over the test concentration range (0.01 μM, 0.1 μM, 1 μM, 10 μM) was added and incubated with the cells for 24 hours. By using Bright-Glo (Promega) as a luciferase assay substrate, and measuring the luminescence intensity with luminometer LB960 (Berthold Technologies), the effect of the test compound on the activation of luciferase transcription via the LXRα- or LXRβ-LBD was measured. T0901317 (the compound of Example 12 of WO2000/54759) was assessed at the same time as a comparative compound. The luciferase activity results are shown in FIGS. 1 and 2 as activity values (% eff) at the respective concentration of the test compound, relative to the T0901317 luminescence intensity of 100 at 10 μM.

<Results>

As shown in FIGS. 1 and 2, it was confirmed experimentally that the 1,3-dihydroisobenzofuran derivative of the present invention is an LXR agonist having a higher selectivity to LXRβ than T0901317 which is a control agent.

The invention claimed is:
1. A 1,3-dihydroisobenzofuran derivative represented by the following general formula (1) or salt thereof:

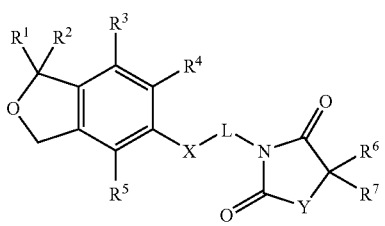

(1)

(wherein $R^1$ and $R^2$ are either same or different and represent a $C_{1-8}$ alkyl group or halo $C_{1-8}$ alkyl group; $R^3$, $R^4$, and $R^5$ are either same or different and represent a hydrogen atom, halogen atom, $C_{1-8}$ alkyl group, halo $C_{1-8}$ alkyl group, $C_{2-8}$ alkenyl group, $C_{2-8}$ alkynyl group, $C_{1-8}$ alkoxy group, $C_{1-8}$ acyl group, nitro group, cyano group, carboxyl group, carbamoyl group, or $C_{6-10}$ aryl $C_{1-8}$ alkyl group, wherein the $C_{6-10}$ aryl may have 1 to 3 substituents selected from the following group A; $R^6$ and $R^7$ are either same or different and represent a hydrogen atom, $C_{1-8}$ alkyl group, $C_{3-8}$ cycloalkyl group, halo $C_{1-8}$ alkyl group, $C_{6-10}$ aryl group or 5- to 11-membered heterocyclic group, wherein the $C_{6-10}$ aryl group and 5- to 11-membered heterocyclic group may have 1 to 3 substituents selected from the following group A, and $R^6$ and $R^7$ may together form a $C_{3-8}$ alkyl ring; L represents a $C_{2-10}$ alkyl chain, $C_{2-10}$ alkenyl chain, or $C_{2-6}$ alkyl-O—$C_{2-6}$ alkyl chain; X represents a —O— or —N($R^8$)—; $R^8$ represents a hydrogen atom or $C_{1-8}$ alkyl group; Y represents an O, S, —CH($R^9$)—, —CH$_2$CH($R^{10}$)—, —CH$_2$O—, or —N($R^{11}$)—; $R^9$ and $R^{10}$ are either same or different and represent a hydrogen atom or $C_{1-8}$ alkyl group; $R^{11}$ represents a hydrogen atom, $C_{1-8}$ alkyl group that may be substituted with a $C_{1-8}$ alkoxycarbonyl group, halo $C_{1-8}$ alkyl group, $C_{6-10}$ aryl group, or 5- to 11-membered heterocyclic group, wherein the $C_{6-10}$ aryl group and 5- to 11-membered heterocyclic group may have 1 to 3 substituents selected from the following group A), [Group A: halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, $C_{1-8}$ alkoxy group, halo $C_{1-8}$ alkoxy group, $C_{1-8}$ acyl group, nitro group, amino group, mono $C_{1-6}$ alkylamino group, di $C_{1-6}$ alkylamino group, cyano group, hydroxy group, carboxyl group, $C_{1-8}$ alkoxycarbonyl group, carbamoyl group, $C_{6-10}$ aryl group, 5- to 11-membered heterocyclic group, $C_{1-6}$ alkylthio group, $C_{1-6}$ alkylsulfonyl group, $C_{6-10}$ arylthio group, $C_{6-10}$ arylsulfonyl group, tetrahydropyranyloxy group, and $C_{1-6}$ alkylenedioxy group].

2. A medicine composition comprising a therapeutically effective amount of the 1,3-dihydroisobenzofuran derivative or salt thereof according to claim 1 as an active ingredient.

3. The medicine composition according to claim 2, which is a therapeutic agent for atherosclerosis, arteriosclerosis resulting from diabetes, dyslipidemia, hypercholesterolemia, diabetes, or Alzheimer's disease.

4. An LXR regulator containing the 1,3-dihydroisobenzofuran derivative or salt thereof according to claim 1 as an active ingredient.

5. A pharmaceutical composition comprising the 1,3-dihydroisobenzofuran derivative or salt thereof according to claim 1 and a pharmaceutically acceptable carrier.

6. A method for treating atherosclerosis, arteriosclerosis resulting from diabetes, dyslipidemia, hypercholesterolemia, diabetes, or Alzheimer's disease, in a subject in need thereof, comprising administering to said subject a therapeutically effective amount of the 1,3-dihydroisobenzofuran derivative or salt thereof according to claim 1.

7. A medicine composition according to claim 2, wherein the medicine composition is administered in the form of an oral preparation, injection, suppository, ointment, inhalation, eye-drops, nasal preparation, or adhesive patch.

8. The LXR regulator according to claim 4, wherein said LXR regulator has a higher selectivity for activating LXRβ expression than a LXRα expression.

\* \* \* \* \*